United States Patent
Gu et al.

(10) Patent No.: US 11,274,142 B2
(45) Date of Patent: Mar. 15, 2022

(54) FUSION PROTEIN CONTAINING TGF-β RECEPTOR AND MEDICINAL USES THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Jinming Gu, Shanghai (CN); Xiao Luo, Shanghai (CN); Weikang Tao, Shanghai (CN)

(73) Assignees: Jiangsu Hengrui Medicine Co., Ltd., Jiangsu (CN); Shanghai Hengrui Pharmaceutical Co., Ltd., Shanhai (CN)

( * ) Notice: Subject to any disclaimer, the term of this patent is extended or adjusted under 35 U.S.C. 154(b) by 56 days.

(21) Appl. No.: 16/610,585

(22) PCT Filed: May 11, 2018

(86) PCT No.: PCT/CN2018/086451
§ 371 (c)(1),
(2) Date: Nov. 4, 2019

(87) PCT Pub. No.: WO2018/205985
PCT Pub. Date: Nov. 15, 2018

(65) Prior Publication Data
US 2020/0157180 A1    May 21, 2020

(30) Foreign Application Priority Data
May 12, 2017 (CN) .......................... 201710334292.6

(51) Int. Cl.
| | |
|---|---|
| *A61K 39/395* | (2006.01) |
| *C07K 19/00* | (2006.01) |
| *C07K 14/71* | (2006.01) |
| *C07K 16/32* | (2006.01) |
| *A61P 35/00* | (2006.01) |
| *C07K 16/28* | (2006.01) |

(52) U.S. Cl.
CPC .............. *C07K 14/71* (2013.01); *A61P 35/00* (2018.01); *C07K 16/2827* (2013.01); *C07K 16/32* (2013.01); *C07K 2317/24* (2013.01); *C07K 2317/51* (2013.01); *C07K 2317/565* (2013.01); *C07K 2319/03* (2013.01); *C07K 2319/10* (2013.01)

(58) Field of Classification Search
None
See application file for complete search history.

(56) References Cited

U.S. PATENT DOCUMENTS

| | | |
|---|---|---|
| 2010/0204104 A1 | 8/2010 | Qiu et al. |
| 2015/0056199 A1 | 2/2015 | Kumar et al. |

FOREIGN PATENT DOCUMENTS

| | | |
|---|---|---|
| WO | 2006074451 A3 | 3/2007 |
| WO | 2011109789 A2 | 9/2011 |
| WO | 2011109789 A3 | 4/2012 |
| WO | 2013164694 A1 | 11/2013 |
| WO | 2014164427 A1 | 10/2014 |
| WO | 2015027082 A1 | 2/2015 |
| WO | 2015118175 A2 | 8/2015 |
| WO | 2015118175 A3 | 10/2015 |
| WO | 2015077540 A3 | 11/2015 |
| WO | 2016011003 A1 | 1/2016 |
| WO | 2018035119 A2 | 2/2018 |

OTHER PUBLICATIONS

Int'l Search Report and Written Opinion dated Aug. 1, 2018 in Int'l Application No. PCT/CN2018/086451, translation of ISR only.
Supplementary European Search Report for European Patent Application No. 18 79 8641, issued by the European Patent Office, including Annex, 3 pages.

*Primary Examiner* — Christine J Saoud
*Assistant Examiner* — Jon M Lockard
(74) *Attorney, Agent, or Firm* — Ice Miller LLP

(57) ABSTRACT

The present invention provides a fusion protein containing TGF-β receptor and pharmaceutical use thereof. Further, the present invention provides a bifunctional fusion protein comprising the PD-L1 antibody targeting portion and the TGF-βRII extracellular domain, and a pharmaceutical composition comprising the fusion protein containing TGF-β receptor, and the use thereof in the preparation of anti-cancer drug.

Figure 1:
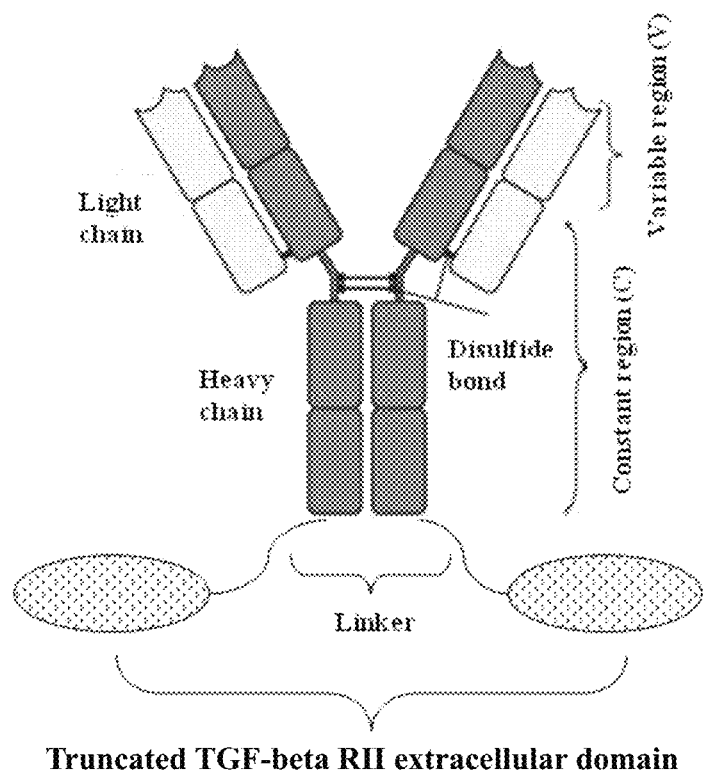

16 Claims, 5 Drawing Sheets
Specification includes a Sequence Listing.

FUSION PROTEIN CONTAINING TGF-β RECEPTOR AND MEDICINAL USES THEREOF

CROSS-REFERENCE TO RELATED APPLICATION

This application is a Section 371 of International Application No. PCT/CN2018/086451, filed May 11, 2018, which was published in the Chinese language on Nov. 15, 2018, under International Publication No. WO 2018/205985 A1, which claims priority under 35 U.S.C. § 119(b) to Chinese Application No. 201710334292.6, filed May 12, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing_688452_127US" and a creation date of Oct. 17, 2019, and having a size of 32.1 kb. The sequence listing submitted via EFS-Web is part of the specification and is herein incorporated by reference in its entirety.

FIELD OF THE INVENTION

The present invention relates to the field of tumor immunotherapy drugs. In particular, the invention relates to fusion proteins for the treatment of cancer, involving a fusion protein comprising a targeting molecule and an immunomodulatory factor (such as TGF-βRII). More specifically, the present invention relates to a fusion protein formed by a targeting molecule anti-PD-L1 antibody and an immunomodulatory factor (such as TGF-βRII), a pharmaceutical composition comprising the same, and its use as an anticancer drug.

BACKGROUND OF THE INVENTION

In the treatment of cancer, people have recognized the high toxicity caused by chemotherapy and the negative effects that can lead to drug-resistant cancer cells. Even if the treatment targeted overexpressed or activated proteins which are associated with tumor survival, cancer cells would still rely on mutations to reduce or escape the dependence on the pathways which are targeted by the therapy, and would also survive via other pathways. Tumor immunotherapy received much attention in recent years and is the focus of cancer treatment. It is difficult to develop drug resistance, and this is the outstanding advantage of this therapy. Based on immunological theory and method, tumor immunotherapy mainly enhances the immunogenicity of tumor cells and the sensitivity to effector cell killing, stimulates and enhances the anti-tumor immune response, and injects immune cells and effector molecules into the host to coordinate with the immune system to kill tumor cell and inhibit tumor growth.

Programmed death protein 1 (PD-1) is a member of the CD28 superfamily. PD-1 is expressed on activated T cells, B cells and myeloid cells, which have two ligands, PD-L1 (programmed death ligand 1) and PD-L2. PD-L1 interacts with PD-1 on T cells and plays an important role in the negative regulation of immune responses. The expression of protein PD-L1 can be detected in many human tumor tissues. Tumor microenvironment can induce the expression of PD-L1 on tumor cells. The expression of PD-L1 is beneficial to the occurrence and growth of tumors, and induces apoptosis of anti-tumor T cells. PD-1/PD-L1 pathway inhibitors can block the binding of PD-1 to PD-L1 leading to a block in the negative regulatory signal, and restoration of T cell activity to enhance the immune response. Therefore, immunoregulation targeting PD-1/PD-L1 is important for tumor suppression.

Transforming growth factor-0 (TGF-β) belongs to the TGF-β superfamily that regulates cell growth and differentiation. TGF-β transmits signal through a heterotetrameric receptor complex which is composed of two type I and two type II transmembrane serine/threonine kinase receptors.

TGF-β is a multifunctional cytokine that exerts tumor suppressor or tumor-promoting effects in a cell-dependent or background-dependent manner. The tumor suppressive effect of TGF-β signaling is due to the ability to induce expression of multiple genes. When a mutation or epigenetic modification occurs during tumor development, cancer cells gradually tolerate the inhibition of TGF-β signaling, which ultimately leads to the development of tumors.

Studies have found that blocking the TGF-β signaling pathway can reduce tumor metastasis. A truncated Smad2/3 dominant negative mutant was used to inhibit the TGF-β signaling pathway of the breast tumor cell line, and it was found that the metastatic ability of the tumor cells was inhibited. Microsatellite instability studies of colon cancer found that inactive mutations of TGF-βRII reduced metastasis and increased postoperative survival. However, in general, the use of a TGF-β signaling pathway inhibitor alone has a weak effect in clinical treatment, which may be related to the high expression of TGF-β in tumor cells and the bioavailability of signaling pathway inhibitors.

Therefore, inhibiting the PD-1/PD-L1 pathway based on blocking and neutralizing TGF-β in the tumor microenvironment can restore T cell activity, enhance immune responses, and improve the effect of inhibiting tumor occurrence development. An anti-PD-L1 antibody is provided by the applicant's prior PCT application PCT/CN2016/104320.

Up to date, there have been antibody/TGF-β receptor fusion proteins disclosed in WO2006074451A2, WO2009152610A1, WO2011109789A2, WO2013164694A1, WO2014164427A1, WO2015077540A2, WO9309228A1, WO9409815A1, WO2015077540A2, WO2015118175A2. However, some fusion proteins still have problems of instability or low expression. There is still a need to further develop products with better performance in both production and clinical practice. The present invention provides a technical solution which benefits production and has more stable performance.

SUMMARY OF THE INVENTION

The present invention provides a fusion protein containing a TGF-β receptor, comprising a targeting moiety and a TGF-β receptor moiety, wherein the TGF-β receptor moiety is an N-terminal truncated form of the extracellular domain of TGF-βRII.

In a preferred embodiment of the present invention, the N-terminal truncated form of the extracellular domain of TGF-βRII involves a deletion of 26 or fewer contiguous amino acids at the N-terminus of the extracellular domain of TGF-βRII, preferably a deletion of 14-26 contiguous amino acids, more preferably a deletion of 14-21 contiguous amino acids, most preferably a deletion of 14-21 contiguous amino acids. As non-limiting examples, the N-terminal truncated form of the extracellular domain of TGF-βRII comprises the sequence of SEQ ID NO: 14 or SEQ ID NO: 15.

In a preferred embodiment of the present invention, the sequence of extracellular domain of TGF-βRII is shown as SEQ ID NO: 13.

In a preferred embodiment of the present invention, the targeting moiety is a cell-specific targeting moiety; preferably, the targeting moiety is a cancer cell-specific targeting moiety.

In a preferred embodiment of the present invention, the cancer cell-specific targeting moiety is selected from the group consisting of an antibody or antigen-binding fragment thereof, a growth factor, a hormone, a peptide, a receptor and a cytokine.

In a preferred embodiment of the present invention, the antibody or antigen-binding fragment thereof is selected from the group consisting of a full length antibody, a chimeric antibody, Fab', Fab, F(ab')2, a single domain antibody (DAB), Fv, scFv, a small antibody, a bispecific antibody, and a tri-specific antibody or mixture thereof.

In a preferred embodiment of the present invention, the antibody or antigen-binding fragment thereof binds to one or more of the following polypeptides or proteins selected from the group consisting of HER2, HER3, immune checkpoint molecule, CD33, VEGF, VEGFR, VEGFR-2, CD152, TNF, IL-1, IL-5, IL-17, IL-6R, IL-1, IL-2R, BLYS, PCSK9, EGFR, c-Met, CD2, CD3, CD11a, CD19, CD30, CD38, CD20, CD52, CD60, CD80, CD86, TNF-α, IL-12, IL-17, IL-23, IL-6, IL-1β, RSVF, IgE, RANK, BLyS, α4β7, PD-1, CCR4, SLAMF7, GD2, CD21, CD79b, IL20Rα, CD22, CD79a, CD72, IGF-1R and RANKL; preferably the antibody or antigen-binding fragment thereof binds to an immune checkpoint molecule.

In a preferred embodiment of the present invention, the antibody is an anti-PD-L1 antibody; preferably, the anti-PD-L1 antibody is selected from the group consisting of: MSB0010718C, MEDI4736, BMS-936559 and MPDL3280A; or the anti-PD-L1 antibody comprises one or more CDR(s) selected from the group consisting of the below or the mutant thereof:

```
HCDR1:
                                           SEQ ID NO: 1
SYWMH

HCDR2:
                                           SEQ ID NO: 2
RI X1PNSG X2TSYNEKFKN

HCDR3:
                                           SEQ ID NO: 3
GGSSYDYFDY

LCDR1:
                                           SEQ ID NO: 4
RASESVSIHGTHLMH

LCDR2:
                                           SEQ ID NO: 5
AASNLES

LCDR3:
                                           SEQ ID NO: 6
QQSFEDPLT;
``` wherein $X_1$ is H or G, preferably G; $X_2$ is G or F, preferably F.

In a preferred embodiment of the present invention, the antibody or antigen-binding fragment thereof is a chimeric antibody or a functional fragment thereof, a humanized antibody or a functional fragment thereof, or a human antibody or a functional fragment thereof.

In a preferred embodiment of the present invention, the humanized antibody comprises a heavy chain variable region of SEQ ID NO: 7, preferably comprises a heavy chain variable region of SEQ ID NO: 9.

In a preferred embodiment of the present invention, the humanized antibody further comprises a heavy chain of SEQ ID NO: 11.

In a preferred embodiment of the present invention, the humanized antibody comprises a light chain variable region of SEQ ID NO: 8 or 10 or the mutant thereof.

In a preferred embodiment of the present invention, the humanized antibody comprises a light chain of SEQ ID NO: 12.

In a preferred embodiment of the present invention, the fusion protein comprising TGF-β receptor is as shown in the general formula (I):

$$\text{Ab-L-TGF-βRII ECD} \tag{I}$$

wherein the TGF-βRII ECD is a truncated form of the extracellular domain of TGF-βRII;
Ab is an antibody;
L is a linker.

In a preferred embodiment of the present invention, the linker is $(G_4S)_xG$, wherein x is 3-6, preferably is 4-5.

The present invention further provides a pharmaceutical composition, comprising a therapeutically effective amount of a fusion protein containing a TGF-β receptor as described above, and one or more pharmaceutically acceptable carrier(s), diluent(s) or excipient(s).

The present invention further provides DNA molecule encoding the fusion protein comprising a TGF-β receptor as described above.

The present invention further provides an expression vector, comprising the DNA molecule as described above.

The present invention further provides a host cell transformed with the expression vector as described above, wherein the host cell is selected from the group consisting of a bacterial, yeast, and mammalian cell; preferably a mammalian cell.

The present invention further provides a use of the fusion protein containing a TGF-β receptor as described above or the pharmaceutical composition thereof for the preparation of a medicament for the treatment of tumors; preferably for preparation of a medicament for treating a PD-L1-mediated tumor; more preferably a cancer expressing PD-L1.

The present invention further provides a method for treating or preventing a tumor comprising administering to a patient in need thereof a therapeutically effective amount of the fusion protein containing a TGF-β receptor as described above.

The present invention further provides a truncated extracellular domain of TGF-βRII, wherein the truncated extracellular domain of TGF-βRII involves a deletion of 26 or fewer contiguous amino acids at the N-terminus of SEQ ID NO: 13, preferably a deletion of 14-26 contiguous amino acids at the N-terminus, more preferably a deletion of 14-21 contiguous amino acids at the N-terminus; the non-limiting examples of the truncated extracellular domain of TGF-βRII comprises sequence shown as SEQ ID NO: 14 or SEQ ID NO: 15.

The present invention further provides a pharmaceutical composition, comprising a therapeutically effective amount of a truncated extracellular domain of TGF-βRII of the present invention, and one or more pharmaceutically acceptable carrier(s), diluent(s) or excipient(s).

The present invention further provides a use of the truncated extracellular domain of TGF-βRII of the present invention or a pharmaceutical composition thereof for the preparation of a medicament for the treatment or inhibition of diseases or disorders associated with cancer cell proliferation or metastasis.

The present invention further provides a method for treating or preventing a tumor comprising administering to a patient in need thereof a therapeutically effective amount of the truncated extracellular domain of TGF-βRII of the present invention or the pharmaceutical composition thereof.

The tumor or cancer described in the present disclosure is selected from the group consisting of colorectal, breast, ovary, pancreas, stomach, prostate, kidney, cervix, myeloma, lymphoma, leukemia, thyroid, endometrium, uterus, bladder, neuroendocrine, head and neck, liver, nasopharynx, testis, small cell lung cancer, non-small cell lung cancer, melanoma, basal cell skin cancer, squamous cell skin cancer, dermatofibrosarcoma protuberans, Neck Cell carcinoma, glioblastoma, glioma, sarcoma, mesothelioma, and myelodysplastic syndrome.

DRAWING DESCRIPTION

FIG. 1: Schematic diagram of the structure of the fusion protein.

Figure 2:
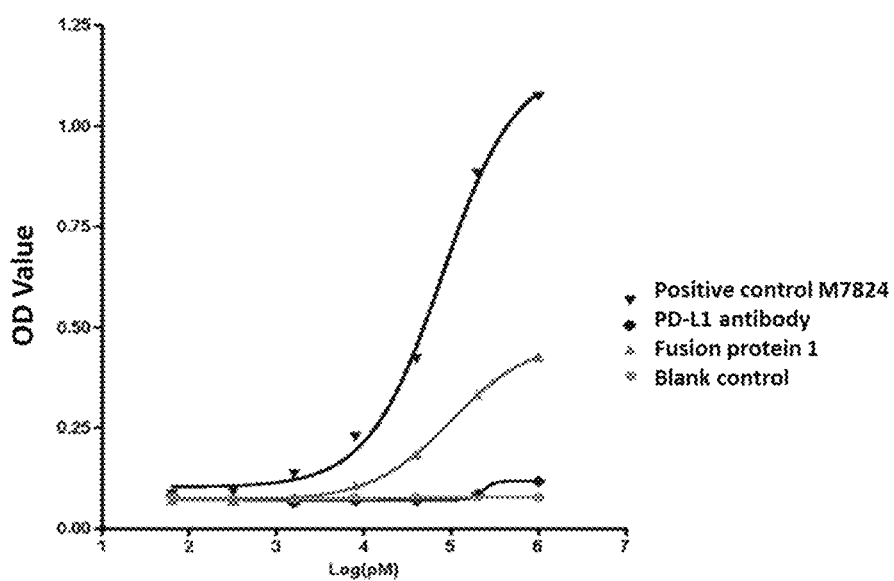

FIG. 2: Results showing the binding of fusion protein to human TGF-β1 in vitro.

Figure 3:
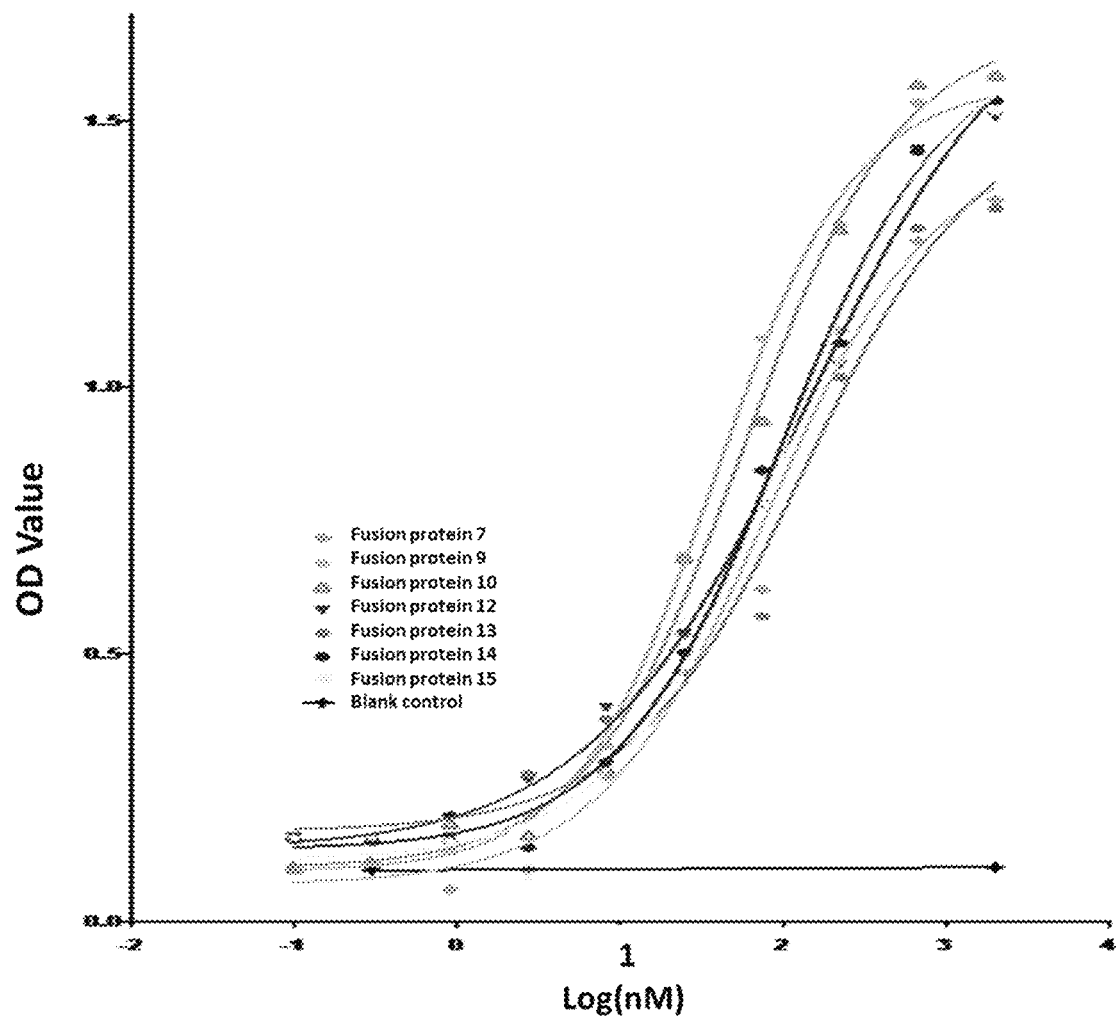

FIG. 3: Results showing the binding of fusion protein to human TGF-β1 in vitro.

Figure 4:
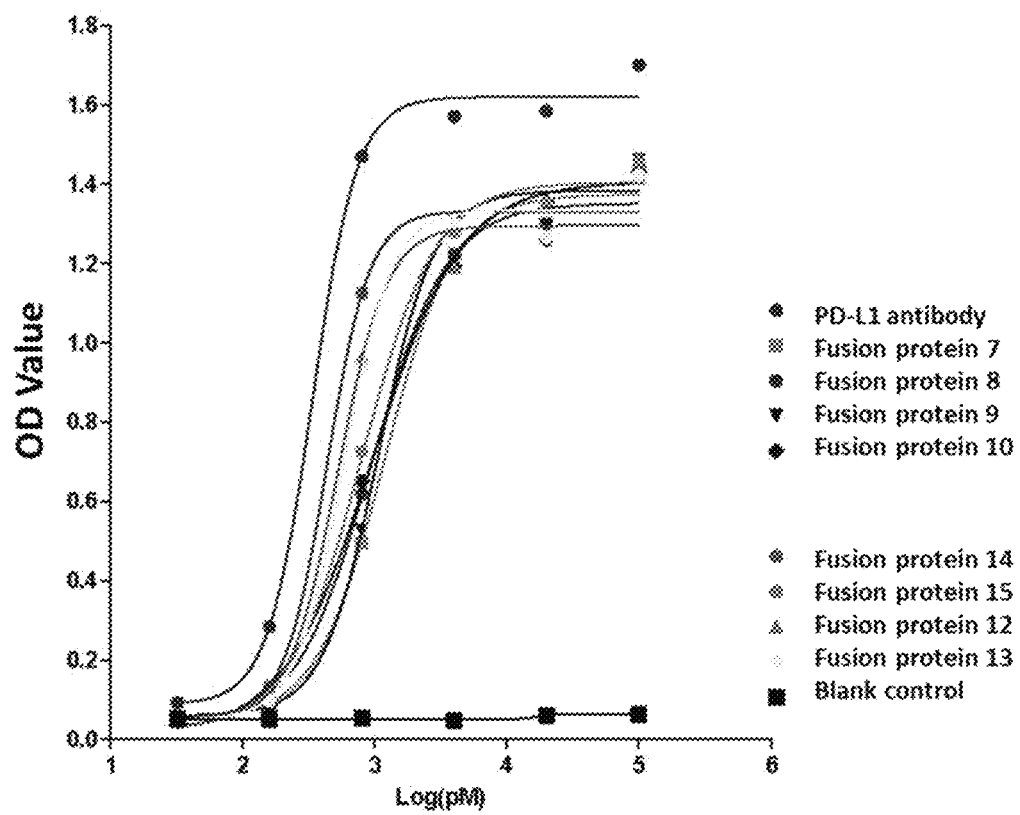

FIG. 4: Results showing the binding of fusion protein to human PD-L1 in vitro.

Figure 5:
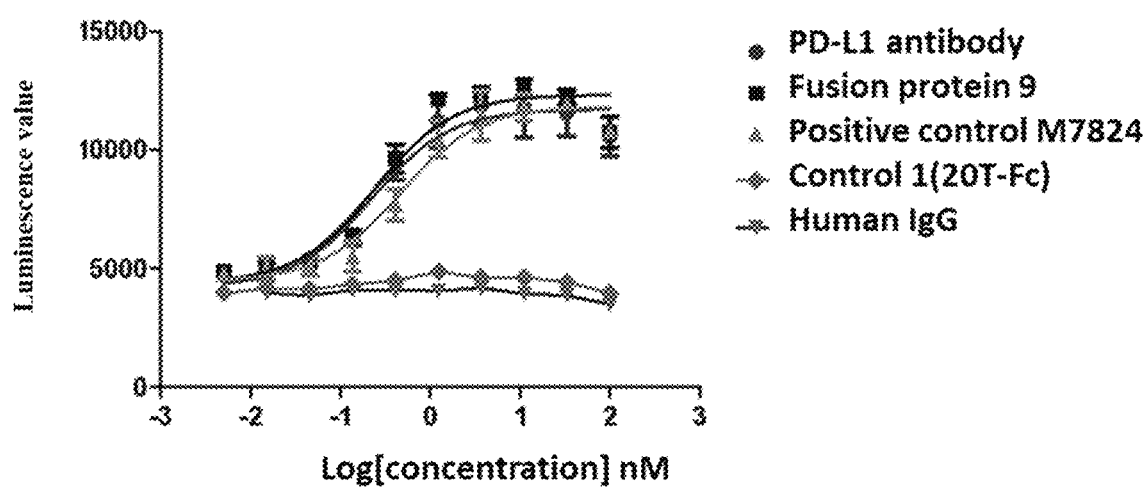

FIG. 5: Result showing the detection of PD-1/PD-L1 pathway blocking by fusion protein in vitro.

Figure 6:
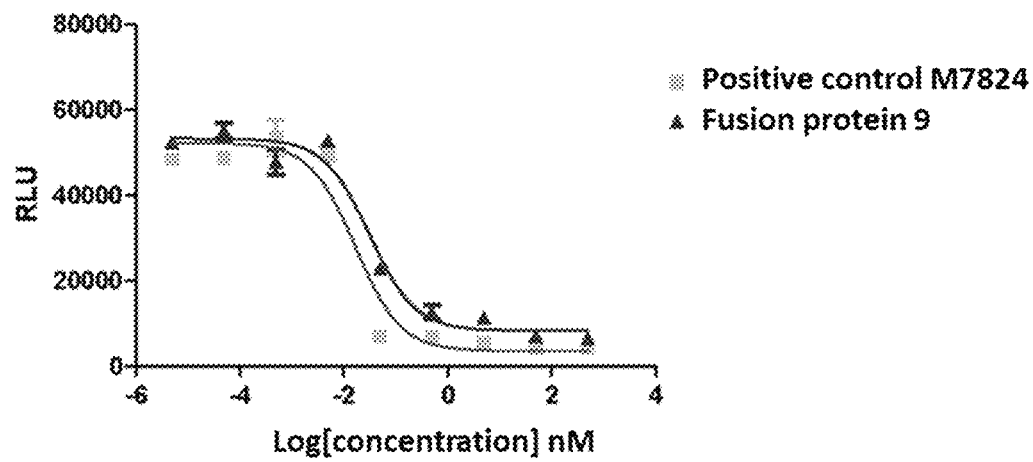

FIG. 6: Fusion protein inhibits TGFβ-induced pSMAD3 reporter activity in a dose-dependent manner.

Figure 7:
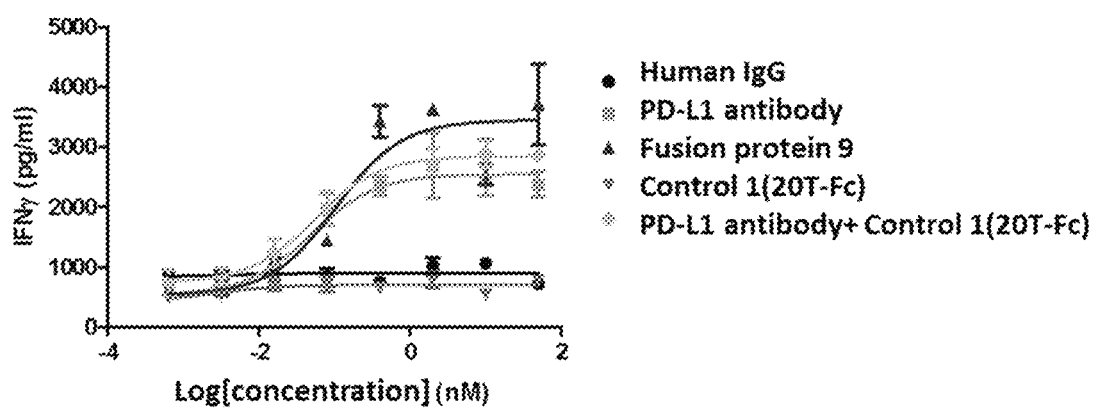

FIG. 7: All fusion protein samples enhance the secretion of the cytokine IFN-γ by activated T lymphocytes.

Figure 8:
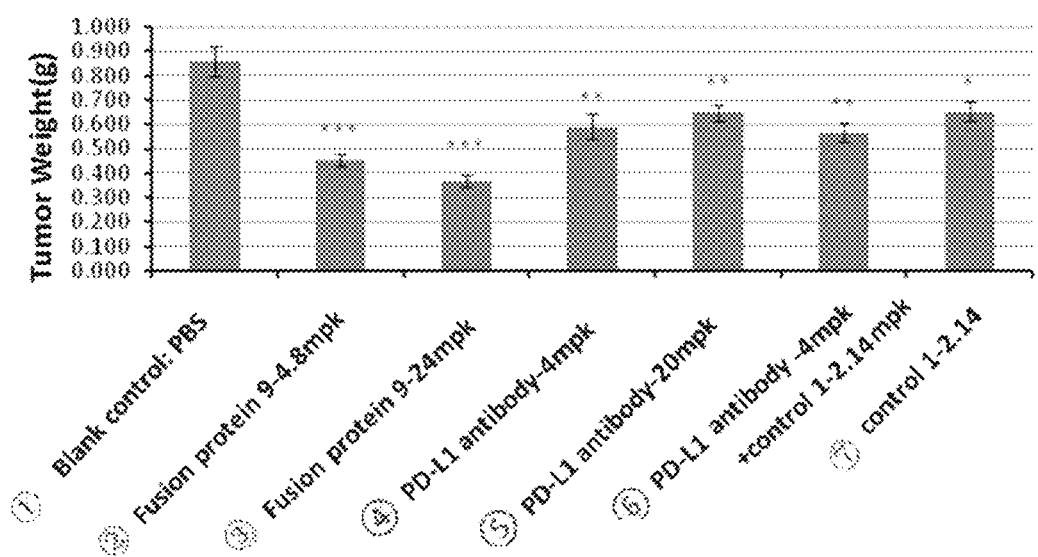

FIG. 8: Effect of fusion protein on tumor weight of tumor-bearing mice.

DETAILED DESCRIPTION OF THE INVENTION

Terms

For the invention to be more readily understood, certain technical and scientific terms are specifically defined below. Unless specifically defined elsewhere herein, all other technical and scientific terms used herein have the meaning commonly understood by one of ordinary skills in the art to which this invention pertains.

As used herein, the single-letter code and the three-letter code for amino acids are as described in J. Biol. Chem, 243, (1968) p3558.

As used herein, "antibody" refers to immunoglobulin, a four-peptide chain structure formed by two identical heavy chains and two identical light chains connected by inter-chain disulfide bond. Different immunoglobulin heavy chain constant regions exhibit different amino acid compositions and sequences, hence present different antigenicity. Accordingly, immunoglobulins can be divided into five categories, also referred as immunoglobulin isotypes, namely IgM, IgD, IgG, IgA and IgE; the corresponding heavy chains thereof are μ chain, δ chain, γ chain, α chain, ε chain, respectively. According to amino acid composition of hinge region and the number and location of heavy chain disulfide bonds, immunoglobulins can be divided into different sub-categories, for example, IgG can be divided into IgG1, IgG2, IgG3, and IgG4. Light chain can be divided into κ or λ chain, based on different constant regions. Each category of Ig among these five categories involves κ or λ chain.

In the present invention, the antibody light chain mentioned herein further comprises a light chain constant region, which comprises a human or murine κ, λ chain or a variant thereof.

In the present invention, the antibody heavy chain mentioned herein further comprises a heavy chain constant region, which comprises human or murine IgG1, IgG2, IgG3, IgG4 or a variant thereof.

At the N-terminal of the antibody heavy and light chains, about 110 amino acids vary largely, which is known as the variable region (Fv region); the amino acid sequence at the C-terminus is relatively stable, which is known as the constant region. The variable region comprises three hypervariable regions (HVR) and four framework regions (FRs) with relatively conserved sequence. Three hypervariable regions determine the specificity of the antibody, also known as complementarity determining region (CDR). Each light chain variable region (LCVR) and each heavy chain variable region (HCVR) is composed of three CDR regions and four FR regions, arranged from the amino terminal to the carboxyl terminal: FR1, CDR1, FR2, CDR2, FR3, CDR3, and FR4. Three light chain CDR regions refer to LCDR1, LCDR2, and LCDR3; three heavy chain CDR regions refer to HCDR1, HCDR2 and HCDR3. The number and location of CDR region amino acid residues in LCVR and HCVR regions of the antibody or antigen binding fragment herein comply with known Kabat numbering criteria (LCDR1-3, HCDR2-3), or comply with kabat and chothia numbering criteria (HCDR1).

The antibody of the present invention comprises a full-length antibody selected from the group consisting of a murine antibody, a chimeric antibody and a humanized antibody, preferably the antibody is a humanized antibody.

The term "murine antibody" in the present invention refers to an anti-human PD-L1 monoclonal antibody prepared according to the knowledge and skills in the field. During the preparation, a test subject was injected with a PD-L1 antigen, and then a hybridoma expressing an antibody which possesses a desired sequence or functional characteristics was isolated. In a preferred embodiment of the present invention, the murine anti-PD-L1 antibody or antigen binding fragment thereof, further comprises light chain constant region of murine κ, λ chain or a variant thereof, or further comprises heavy chain constant region of murine IgG1, IgG2, IgG3 or a variant thereof.

The term "chimeric antibody", is an antibody which is formed by fusing the variable region of a murine antibody with the constant region of human antibody, so as to alleviate the murine antibody-induced immune response. To establish a chimeric antibody, a hybridoma secreting specific murine monoclonal antibody is first established, variable region genes are then cloned from murine hybridoma cells, and then constant region genes of a human antibody are cloned as desired. The murine variable region genes are ligated with human constant region genes to form a chimeric gene which can be inserted into a human vector, and finally the chimeric antibody molecule is expressed in a eukaryotic or prokaryotic industrial system. In a preferred embodiment of the present invention, the light chain of the anti-PD-L1 chimeric antibody further comprises the light chain constant regions derived from human κ, λ chain or a variant thereof.

The heavy chain of the anti-PD-L1 chimeric antibody further comprises the heavy chain constant region(s) derived from human IgG1, IgG2, IgG3, IgG4 or a variant thereof. The constant region(s) of the human antibody can be selected from heavy chain constant region(s) derived from human IgG1, IgG2, IgG3, IgG4 or a variant thereof, preferably comprises heavy chain constant region derived from human IgG2 or IgG4, or IgG4 without ADCC (antibody-dependent cell-mediated cytotoxicity) after amino acid mutation.

The term "humanized antibody", also known as CDR-grafted antibody, refers to an antibody generated by murine CDR sequences grafted into human antibody variable region framework, i.e. antibody generated from different types of sequences of human germline antibody framework. Humanized antibodies conquer the disadvantageously strong anti-antibody response induced by chimeric antibodies which carry a large number of murine components. Such framework sequences can be obtained from public DNA database covering germline antibody gene sequences or published references. For example, germline DNA sequences of human heavy and light chain variable region genes can be found in "VBase" human germline sequence database (available on web www.mrccpe.com.ac.uk/vbase), as well as found in Kabat, E A, et al. 1991 Sequences of Proteins of Immunological Interest, 5th Ed. To avoid the decrease in activity caused by reduction of immunogenicity, the variable region framework of the human antibody is subjected to minimum back-mutation to maintain the activity. The humanized antibody of the present invention also comprises a humanized antibody which is further obtained by phage display for the purpose of CDR affinity maturation.

The terms "human antibody" and "antibody from human" are used interchangeably to mean that one or more variable and constant regions are derived from a human immunoglobulin sequence. In a preferred embodiment, all of the variable and constant regions are derived from human immunoglobulin sequences, i.e., "antibodies fully derived from human" or "fully human antibodies." These antibodies can be obtained in a variety of ways, including by phage display technology; isolation of B cells from human PBMC, spleen or lymph nodes; construction of a native single-stranded phage human antibody library; or by immunization of transgenic mice that express human antibody light and heavy chains; and screening thus obtained antibodies.

As used herein, "antigen-binding fragment" or "functional fragment" refers to Fab fragment, Fab' fragment, F(ab')2 fragment with antigen-binding activity, as well as Fv fragment and scFv fragment binding with human PD-L1. Fv fragment is the minimum antibody fragment which involves all antigen-binding sites, Fv fragment comprises a heavy chain variable region and a light chain variable region, but without a constant region. Generally, Fv antibody further comprises a polypeptide linker between the VH and VL domains to form a structure required for antigen binding. Also, different linkers can be used to connect the variable regions of two antibodies to form a polypeptide, named single chain antibody or single chain Fv (scFv). As used herein, the term "binding with PD-L1" means the ability to interact with human PD-L1. As used herein, the term "antigen-binding site" of the present invention refers to discontinuous, three-dimensional sites on the antigen, recognized by the antibody or the antigen-binding fragment of the present invention.

As used herein, the term "ADCC", namely antibody-dependent cell-mediated cytotoxicity, refers to the cells expressing Fc receptors that directly kill the target cells coated by an antibody by recognizing the Fc segment of the antibody. ADCC effector function of the antibody can be reduced or eliminated by modifying the Fc segment in IgG. The modification refers to mutations on the antibody heavy chain constant region, such as mutations selected from N297A, L234A, L235A in IgG1; IgG2/4 chimera; or F234A/L235A mutations in IgG4.

"Mutation" in the "mutant sequence" of the present invention includes, but is not limited to "back mutation", "conservative modification" or "conservative replacement or substitution". "Conservative modification" or "conservative replacement or substitution" in the present disclosure refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skilled in the art recognize that, in general, a single amino acid substitution in a non-essential region of a polypeptide does not substantially alter biological activity (see, e.g., Watson et al. (1987) Molecular Biology of the Gene, The Benjamin/Cummings Pub. Co., p. 224 (4th Ed)). In addition, substitutions of structurally or functionally similar amino acids are less likely to disrupt biological activity.

The "mutant sequence" as used in the present invention means that the nucleotide sequence and the amino acid sequence of the present invention are subjected to substitution, insertion or deletion, thus the obtained nucleotide sequence and amino acid sequence share varying percentage identity with the nucleotide sequence and the amino acid sequence of the present invention.

As used herein, "identity" indicates the degree of similarity between two nucleic acids or two amino acid sequences. The sequence identity in the present invention is at least 85%, 90% or 95%, preferably at least 95%. Representative examples include, but are not limited to, 85%, 86%, 87%, 88%, 89%, 90%, 91%, 92%, 93%, 94%, 95%, 96%, 97%, 98%, 99%, 100%. The comparison of sequences and determination of percent identity between two sequences can be accomplished using the default settings of the BLASTN/BLASTP algorithm available on the National Center for Biotechnology Institute's website.

The "anti-PD-L1 antibody or antigen-binding protein thereof" of the present invention could include any of the anti-PD-L1 antibodies or antigen-binding fragments thereof described in the art. The anti-PD-L1 antibody may be an anti-PD-L1 antibody which is commercially available or has been disclosed in the literature, including, but not limited to, anti-PD-L1 antibody BMS-936559, MPDL3280A, MEDI4736, MSB0010718C (see US2014341917, US20130034559, U.S. Pat. No. 8,779,108) and the like. The antibody may be a monoclonal antibody, a chimeric antibody, a humanized antibody, or a human antibody. The antibody fragment includes Fab fragment, Fab' fragment, F(ab')$_2$ fragment having antigen-binding activity, and Fv fragment and scFv fragment which bind to the antigen.

As an exemplary anti-PD-L1 antibody preparation process of the present invention, see PCT/CN2016/104320, the anti-PD-L1 antibody comprises CDRs of heavy chain variable regions as described below:

HCDR1:
SEQ ID NO: 1
SYWMH

HCDR2:
SEQ ID NO: 2
RI X₁PNSG X₂TSYNEKFKN

HCDR3:
SEQ ID NO: 3
GGSSYDYFDY.

In an alternative embodiment, X₁ is selected from H or G; and X₂ is selected from G or F.

In another embodiment, an exemplary anti-PD-L1 antibody of the invention further comprises CDRs sequence of a light chain variable region as described below:

LCDR1:
SEQ ID NO: 4
RASESVSIHGTHLMH

LCDR2:
SEQ ID NO: 5
AASNLES

LCDR3:
SEQ ID NO: 6
QQSFEDPLT.

In another embodiment, the above CDR regions are humanized by CDR grafting, and the FR of humanized light chain templates are IGKV7-3*01 and hjk2.1, the FR of humanized heavy chain templates are IGHV1-46*01 and hjh6.1, and the humanized variable region sequences are as follows:

humanized heavy chain variable region:

SEQ ID NO: 7
*QVQLVQSGAEVKKPGASVKVSCKASGYTFT*SYWMH*WVRQAPGQGL*

*EWMGR*IX₁PNSGX₂TSYNEKFKN*RVTMTRDTSTSTVYMELSSLRS*

*EDTAVYYCAR*GGSSYDYFDY*WGQGTTVTVSS* humanized light chain variable region:

SEQ ID NO: 8
*DIVLTQSPASLAVSPGQRATITC*RASESVSIHGTHLMH*WYQQKPGQPP*

*KLLIY*AASNLES*GVPARFSGSGSGTDFTLTINPVEANDTANYYC*QQSF

EDPLT*FGQGTKLEIK*

NOTE: The order is FR1-CDR1-FR2-CDR2-FR3-CDR3-FR4, italic portion represents FR sequence, and the underlined portion represents CDR sequence.

In another embodiment, back mutation design on the humanized antibody of the present invention was performed, see the table as follows:

TABLE 1

| VL | | VH | |
|---|---|---|---|
| VL.1 | grafted | VH.1 | grafted |
| VL.1A | Y91F | VH.1A | T74K |
| VL.1B | Y91F, G72E | VH.1B | T74K, R72V, M48I, M70L |
| VL.1C | Y91F, G72E, T22S | VH.1C | T74K, R72V, M48I, M70L, R38Q |
| | | VH.1D | T74K, R72V, M48I, M70L, R38Q, L83F |

TABLE 1-continued

| VL | VH | |
|---|---|---|
| | VH.1E | T74K, R72V, M48I, M70L, R38Q, L83F, V68A, V79A |

Note:
For example, Y91F indicates a back-mutation from Y to F at position 91 according to Kabat numbering system.

"Grafted" indicates that the murine antibody CDR was implanted into human germline FR sequences.

New humanized antibody can be obtained by various combinations of mutations in the heavy chain and light chain shown in the above table.

In another aspect of the invention, an embodiment for construction of a humanized clone is provided, as follows:

Primers were designed, and VH/VK gene fragments of each humanized antibody were constructed by PCR and then inserted into the expression vector pHr (with signal peptide and constant region gene (CH1-Fc/CL) fragment) to perform homologous recombination, in order to construct a full-length antibody expression vector: VH-CH1-Fc-pHr/VK-CL-pHr.

1. Primer Design:

The online software DNAWorks (v3.2.2) (http://helixweb.nih.gov/dnaworks/) was used to design multiple primers for synthesis of VH/VK containing gene fragments required for recombination: 5'-30 bp signal peptide+VH/VK+30 bp CH1/CL-3'.

2. Fragment Splicing:

According to operation instructions for Primer STAR GXL DNA polymerase from TaKaRa Company, using the primers designed above, VH/VK containing gene fragments required for recombination were obtained by two-step PCR amplification.

3. Construction of expression vector pHr (with signal peptide and constant region gene (CH1-FC/CL) fragment) and enzymatic digestion:

The expression vector pHr (with signal peptide and constant region gene (CH1-FC/CL) fragment) was designed and constructed by using some special restriction endonuclease, such as BsmBI which recognizes the distinctive feature between the sequence and restriction site. BsmBI digested the vector, and then the digested fragments were extracted by using gel and stored for use.

4. Recombinant construction of expression vector VH-CH1-Fc-pHr/VK-CL-pHr VH/VK containing gene fragments required for recombination and expression vector pHr (with signal peptide and constant region gene (CH1-FC/CL) fragment) that has been digested with BsmBI were added into DHSH competent cells at a ratio of 3:1, incubated at 0° C. on ice for 30 min, heat-shocked at 42° C. for 90 s, combined with 5 volumes of LB medium, incubated at 37° C. for 45 min, plated on LB-Amp plate, and cultured at 37° C. overnight. Single clone was picked for sequencing and a clone of interest was obtained.

5. The plasmid was constructed according to the design of the present example, then the purified protein, and the affinity of the obtained protein was measured by the detection described in Example SPR.

6. Finally, the affinity of the humanized back-mutation mutant or hybridoma antibodies to human PD-L1-his was measured by BIACORE, the obtained humanized back-mutation sites and sequence combination through screening are as follows:

Heavy Chain Variable Region:

SEQ ID NO: 9
*QVQLVQSGAEVKKPGASVKVSCKASGYTFT*<u>SYWMH</u>*WVRQAPGQGLEWM*
*GRIGPNSGFTSYNEKFKN*<u>R</u>*VTMTRDTSTSTVYMELSSLRSEDTAVYYC*
*AR*<u>GGSSYDYFDY</u>*WGQGTTVTVSS* wherein CDR2 is a sequence in which $X_1$ of SEQ ID NO: 7 is G and $X_2$ is F.

Light Chain Variable Region:

SEQ ID NO: 10
*DIVLTQSPASLAVSPGQRATITC*<u>RASESVSIHGTHLMH</u>*WYQQKPGQPP*
*KLLIY*<u>AASNLES</u>*GVPARFSGSGSGTDFTLTINPVEAEDTANYYC*<u>QQSF</u>
<u>EDPLT</u>*FGQGTKLEIK*

NOTE: The order is FR1-CDR1-FR2-CDR2-FR3-CDR3-FR4, italic portion represents FR sequence, and the underlined portion represents CDR sequence.

In another aspect of the present invention, an embodiment for constructing and expressing an anti-PD-L1 human IgG4 type antibody is provided, and further provided is an anti-PD-L1 antibody used for fusion protein construction. The anti-PD-L1 antibody can also be used as a control molecule in the test examples of the present invention.

Since PD-L1 is also expressed in activated T cells, therefore the use of wild-type IgG1 constant regions can cause Fc-mediated effects such as ADCC and CDC, which could result in the reduction of activated T cells. The present invention selects mutated IgG4 to obtain antibodies without ADCC and CDC. The clone obtained by affinity maturation was converted into IgG4 type, and the core hinge region of IgG4 contained S228P mutation, and F234A and L235A mutations were further introduced (mAbs 4:3, 310-318; May/June 2012). At the same time, in order to avoid breakage at the C-terminus of the antibody heavy chain when the linker peptide (which is used to link the extracellular domain of TGF-βRII) was introduced, the last amino acid K of the anti-PD-L1 antibody heavy chain was further mutated to A, so as to increase the stability of the fusion protein. The anti-PD-L1 antibody sequence of the present invention used for fusion protein construction is as follows:

```
PD-L1 antibody heavy chain: IgG4(AA)(S228P)
                                        SEQ ID NO: 11
QVQLVQSGAEVKKPGASVKVSCKASGYTFTSYWMHWVRQAPGQGLEWM
GRIGPNSGFTSYNEKFKNRVTMTRDTSTSTVYMELSSLRSEDTAVYYC
ARGGSSYDYFDYWGQGTTVTVSSASTKGPSVFPLAPCSRSTSESTAAL
GCLVKDYFPEPVTVSWNSGALTSGVHTFPAVLQSSGLYSLSSVVTVPS
SSLGTKTYTCNVDHKPSNTKVDKRVESKYGPPCPPCPAPEAAGGPSVF
LFPPKPKDTLMISRTPEVTCVVVDVSQEDPEVQFNWYVDGVEVHNAKT
KPREEQFNSTYRVVSVLTVLHQDWLNGKEYKCKVSNKGLPSSIEKTIS
KAKGQPREPQVYTLPPSQEEMTKNQVSLTCLVKGFYPSDIAVEWESNG
QPENNYKTTPPVLDSDGSFFLYSRLTVDKSRWQEGNVFSCSVMHEALH
NHYTQKSLSLSLGA
```

```
PD-L1 antibody light chain:
                                        SEQ ID NO: 12
DIVLTQSPASLAVSPGQRATITCRASESVSIHGTHLMHWYQQKPGQPP
KLLIYAASNLESGVPARFSGSGSGTDFTLTINPVEAEDTANYYCQQSF
EDPLTFGQGTKLEIKRTVAAPSVFIFPPSDEQLKSGTASVVCLLNNFY
PREAKVQWKVDNALQSGNSQESVTEQDSKDSTYSLSSTLTLSKADYEK
HKVYACEVTHQGLSSPVTKSFNRGEC
```

NOTE: The underlined portion is a variable region sequence of the antibody heavy or light chain, or the encoding nucleotide sequence thereof; The remaining portion is antibody constant region sequence and the encoding nucleotide sequence thereof.

As used herein, a fusion protein described in the present invention is a protein product obtained by co-expressing two genes via DNA recombination technology. Methods for producing and purifying antibodies and antigen-binding fragments are well known in the art and can be found, for example, in Antibodies, A Laboratory Manual, Cold Spring Harbor, chapters 5-8 and 15. For example, mice can be immunized with human PD-L1 or fragments thereof, and the resulting antibodies can then be renatured, purified, and sequenced for amino acid sequences by using conventional methods well known in the art. Antigen-binding fragments can also be prepared by conventional methods. The antibody or antigen binding fragments of the present invention are engineered to graft CDRs derived from non-human antibody into one or more human FRs. By aligning against the database of IMGT human antibody variable region germline using MOE software, human framework germline sequences can be obtained from ImMunoGeneTics (IMGT) website http://imgt.cines.fr, or from The Immunoglobulin Facts Book, 2001, ISBN 012441351.

The engineered antibodies or antigen binding fragments of the present invention may be prepared and purified using known methods. For example, cDNA sequences encoding a heavy chain and a light chain may be cloned and engineered into a GS expression vector. The engineered immunoglobulin expression vector may then be stably transfected in CHO cells. As a more recommended method known in the art, mammalian expression systems will result in glycosylation of an antibody, typically at highly conserved N-terminal sites in the Fc region. Stable clones may be obtained by expression of an antibody specifically binding to human PD-L1. Positive clones may be expanded in serum-free culture medium for antibody production in bioreactors. Culture medium, into which the antibody has been secreted, may be purified by conventional techniques. For example, the medium may be loaded onto a Protein A or G Sepharose FF column that has been equilibrated with a compatible buffer. The column is washed to remove nonspecific binding components. The bound antibody is eluted by pH gradient and antibody fractions are detected by SDS-PAGE, and then collected. The antibody may be filtered and concentrated using common techniques. Soluble aggregate and multimers may be effectively removed by common techniques, including size exclusion or ion exchange. The product may be immediately frozen, for example at −70° C., or may be lyophilized.

The "immunomodulatory molecule" of the present invention can be used to attenuate the immune tolerance of cancer cells. The present invention uses a truncated form of the extracellular domain of TGF-βRII as the immunomodulatory molecule in the fusion protein. "TGF-β receptor II (TGF-βRII)" binds ligands TGF-β1 and 3 with high affinity. The TGF-β RII/TGF-β complex recruits TGF-β RI to form a signal transduction complex (Won et al, Cancer Res. 1999; 59: 1273-7). The extracellular domain of TGF-βRII is a 136 amino acid residue peptide from the N-terminus of TGF-βRII extracellular, an exemplary example of which is shown in SEQ ID NO: 13. Other variants of about 136 amino acids in length and derived from the human extracellular domain of TGF-βRII, which are capable of binding to TGF-β1 and 3, also belong to the extracellular domain of TGF-βRII of the invention. The present invention has found that the structure and function of the N-terminal contiguous truncated form of the TGF-βRII extracellular domain is more stable than that of the untruncated molecule. A fusion protein comprising the N-terminal untruncated form of TGF-βRII extracellular domain (a polypeptide shown as aa.1-136 of SEQ ID NO: 13) is susceptible to cleavage. In particular, a truncated form comprising a deletion of at most 26 amino acids at its N-terminus is more stable, preferably a truncation of 14-26 amino acids, more preferably a truncation of 14-21 amino acid at the N-terminus with a higher expression level, most preferably, a truncation of 19 or 21 contiguous amino acids at the N-terminus.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research and experimental methods. Treatment of a cell encompasses contact of a reagent to the cell, as well as contact of a reagent to a fluid, where the fluid is in contact with the cell. "Administration" and "treatment" also mean in vitro and ex vivo treatments, e.g., of a cell, by a reagent, diagnostic, binding compound, or by another cell. "Treatment," as it applies to a human, veterinary, or research subject, refers to therapeutic treatment, prophylactic or preventative measures, to research and diagnostic applications.

"Treat" means to administer a therapeutic agent, such as a composition containing any of the binding compounds of the present invention, internally or externally to a patient having one or more disease symptoms for which the agent has known therapeutic activity. Typically, the agent is administered in an amount effective to alleviate one or more disease symptoms in the patient or population to be treated, to induce the regression of or prevent the progression of such symptom(s) from clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the patient. Whether a disease symptom has been alleviated can be assessed by any clinical measurement typically used by physicians or other skilled healthcare providers to assess the severity or progression status of the symptom. Although an embodiment of the present invention (e.g., a treatment method or article of manufacture) may not be effective in alleviating the target disease symptom(s) in every patient, it should alleviate the target disease symptom(s) in a statistically significant number of patients as determined by any statistical test known in the art such as the Student's t-test, the chi-square test, the U-test according to Mann and Whitney, the Kruskal-Wallis test (H-test), Jonckheere-Terpstra-test and the Wilcoxon-test.

"Conservative modifications" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to disrupt biological activity.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health condition of the patient, the route and dose of administration and the severity of side effects. An effective amount can be the maximal dose or dosing protocol that avoids significant side effects or toxic effects.

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptide sequences. The molecules are deemed as homologous at one position, when this position in both of the sequences to be compared is occupied by the same base or amino acid monomer subunit, e.g., when a position in each of two DNA molecules is occupied by adenine. The percent of homology between two sequences is a function of the number of matching or homologous positions shared by two sequences divided by the number of all positions to be compared and then multiplied by 100. For example, in an optimal alignment, if 6 of 10 positions in two sequences are matched or homologous, then the two sequences share 60% homology. Generally, the comparison is made when two sequences are aligned to give maximum percent homology.

"Immune checkpoint molecules" include stimulatory immune checkpoint molecule and inhibitory immune checkpoint molecule, and exemplary molecules include CD27, CD28, CD40, CD40L, CD122, OX40, OX40L, GITR, ICOS, A2AR, B7-H3, B7-H4, BTLA, CTLA-4, IDO, MR (Killer-cell Immunoglobulin-like Receptor), LAG3, PD-1, PD-L1, PD-L2, TIM-3, VISTA, etc.

As used herein, the expressions "cell," "cell line," and "cell culture" are used interchangeably and all such designations include progeny thereof. Thus, the words "transformant" and "transformed cell" include the primary subject cells and cultures derived therefrom, regardless of the number of passages. It should be also understood that all progeny may not be precisely identical in the aspect of DNA content, due to intentional or unintentional mutations. Mutant progeny that have the same function or biological activity as that of the originally transformed cells are obtained by screening and shall be included in the invention. Where distinct designations are intended, it will be clearly understood from the context.

As used herein, "polymerase chain reaction" or "PCR" refers to a procedure or technique in which small amounts of specific segments of nucleic acid, RNA and/or DNA are amplified as those described in, e.g., U.S. Pat. No. 4,683, 195. Generally, sequence information at the ends of or beyond the region of interest is needed, such that oligonucleotide primers can be designed; the sequence of these primers will be identical or similar to the opposite strand of the template to be amplified. The 5' terminal nucleotides of the two primers coincide with the ends of the material to be amplified. PCR can be used to amplify specific RNA sequences, specific DNA sequences from total genomic DNA, and cDNA transcribed from total cellular RNA, bacteriophage or plasmid sequences, etc. See generally Mullis et al. (1987) Cold Spring Harbor Symp. Ouant. Biol. 51:263; Erlich, ed., (1989) PCR TECHNOLOGY (Stockton Press, N.Y.). The PCR used in the present invention is considered to be one, but not the only, example of polymerase reaction method for amplifying a nucleic acid test sample. The method comprises the use of a known nucleic acids as primers and nucleic acid polymerase to amplify or generate a specific segment of nucleic acid.

"Optional" or "optionally" means that the event or situation that follows may occur, but not necessarily, and the description includes the instances in which the event or circumstance does or does not occur. For example, "optionally contains 1-3 antibody heavy chain variable region(s)" means the antibody heavy chain variable region with specific sequence can be present, but not necessarily.

"Pharmaceutical composition" refers to a mixture comprising one or more compounds according to the present invention or physiologically/pharmaceutically acceptable salt or prodrug thereof and other chemical components, said chemical components are such as physiologically/pharmaceutically acceptable carrier(s) and excipient(s). The pharmaceutical composition aims at promoting the administration by an organism, facilitating the absorption of the active ingredient and thereby exerting biological effect.

EXAMPLES AND TEST EXAMPLES

Hereinafter, the present invention is further described with reference to examples. However, the scope of the present invention is not limited thereto.

In the examples of the present invention, where specific conditions are not described, the experiments are generally conducted under conventional conditions or under conditions proposed by the material or product manufacturers. See Sambrook et al., Molecular Cloning, Laboratory Manual, Cold Spring Harbor Laboratory; Modern Molecular Biology Methods, Ausubel et al., Greene Publishing Association, Wiley Interscience, NY. Where the source of the reagents is not specifically indicated, the reagents are commercially available conventional reagents.

EXAMPLES

Example 1: Fusion Protein PD-L1/TGF-β Trap Cloning and Expression

The TGF-βRII extracellular domain (full length or truncated form of SEQ ID NO: 13) is used as the portion for immunomodulatory molecule in the fusion protein, and the anti-PD-L1 antibody is used as a targeting portion of the fusion protein to form a anti-PD-L1 antibody/TGF-βRII extracellular domain fusion protein (PD-L1/TGF-β trap). Studies have found that the truncated form of the extracellular domain of TGF-βRII is relatively stable, especially when the truncated form involves the deletion of less than 26 amino acids at its N-terminus, preferably a deletion of 14-26 amino acids, more preferably a deletion of 14-21 contiguous amino acids, which exhibits higher expression and stable structure; more preferably a deletion of 14, 19 or 21 contiguous amino acids. The sequences of the non-limiting examples of the TGF-βRII extracellular domain and its truncated form of the invention are as follows:

Sequence of TGF-βRII extracellular domain: ECD (1-136)

SEQ ID NO: 13
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPD

Sequence of truncated TGF-βRII extracellular domain which involves a deletion of 19 contiguous amino acids at N-terminus: ECD (20-136)

SEQ ID NO: 14
GAVFPQLCKFCDVRFSTCDNQKSCMSNCSITSICEKPQEVCVAVWRKN

DENITLETVCHDPKLPYHDFILEDAASPKCIMKEKKKPGETFFMCSC

SSDECNDNIIFSEEYNTSNPD

Sequence of truncated TGF-βRII extracellular domain which involves a deletion of 21 contiguous amino acids at N-terminus: ECD (22-136):

SEQ ID NO: 15
VKFPQLCKFCDVRFSTCDNQKSCMSNCSITSICEKPQEVCVAVWRKND

ENITLETVCHDPKLPYHDFILEDAASPKCIMKEKKKPGETFFMCSCSS

DECNDNIIFSEEYNTSNPD

Sequence of truncated TGF-βRII extracellular domain which involves a deletion of 14 contiguous amino acids at N-terminus: ECD (15-136):

SEQ ID NO: 16
VTDNNGAVKFPQLCKFCDVRFSTCDNQKSCMSNCSITSICEKPQEVCV

AVWRKNDENITLETVCHDPKLPYHDFILEDAASPKCIMKEKKKPGETF

FMCSCSSDECNDNIIFSEEYNTSNPD

The heavy chain C-terminal amino acid of the anti-PD-L1 antibody of the present invention was ligated by linker $(G_4S)_xG$ to the extracellular domain of TGF-βRII with varying lengths by homologous recombination technique, and was conventionally expressed by the 293 expression system together with the light chain, and the obtained fusion proteins are shown in Table 2:

TABLE 2

| PD-L1 antibody/TGF-βRII extracellular domain fusion protein | | |
|---|---|---|
| Fusion protein | Sequence description | the number of contiguous amino acid deleted at N-terminus |
| Fusion protein 1 | Ab-$(G_4S)_4$G-ECD(1-136) | No deletion |
| Fusion protein 2 | Ab-$(G_4S)_3$G-ECD(15-136) | 14 |
| Fusion protein 3 | Ab-$(G_4S)_3$G-ECD(15-136, N19A) | 14 |
| Fusion protein 4 | Ab-$(G_4S)_3$G-ECD(20-136) | 19 |
| Fusion protein 5 | Ab-$(G_4S)_3$G-ECD(22-136) | 21 |

TABLE 2-continued

PD-L1 antibody/TGF-βRII extracellular domain fusion protein

| Fusion protein | Sequence description | the number of contiguous amino acid deleted at N-terminus |
|---|---|---|
| Fusion protein 6 | Ab-(G$_4$S)$_3$G-ECD(27-136) | 26 |
| Fusion protein 7 | Ab-(G4S)$_4$G-ECD(15-136) | 14 |
| Fusion protein 8 | Ab-(G4S)$_4$G-ECD(15-136, N19A) | 14 |
| Fusion protein 9 | Ab-(G4S)$_4$G-ECD(20-136) | 19 |
| Fusion protein 10 | Ab-(G4S)$_4$G-ECD(22-136) | 21 |
| Fusion protein 11 | Ab-(G4S)$_4$G-ECD(27-136) | 26 |
| Fusion protein 12 | Ab-(G$_4$S)$_5$G-ECD(15-136) | 14 |
| Fusion protein 13 | Ab-(G$_4$S)$_5$G-ECD(15-136, N19A) | 14 |
| Fusion protein 14 | Ab-(G$_4$S)$_5$G-ECD(20-136) | 19 |
| Fusion protein 15 | Ab-(G$_4$S)$_5$G-ECD(22-136) | 21 |
| Fusion protein 16 | Ab-(G$_4$S)$_5$G-ECD(27-136) | 26 |
| Fusion protein 17 | Ab-(G$_4$S)$_6$G-ECD(27-136) | 26 |

Note:
Ab represents anti-PD-L1 antibody of the present invention, ECD (n-136) in Sequence Description represents the full-length or truncated form of the extracellular domain of TGF-βRII, n represents the starting number of amino acid after experiencing truncation of the extracellular domain of TGF-βRII. The structure of the fusion protein of the present invention is shown in FIG. 1; N19A indicates that the amino acid at position 19 of the extracellular domain of TGF-βRII was mutated into A.

The nucleotide sequence encoding the anti-PD-L1 antibody, the nucleotide sequence encoding the extracellular domain of TGF-βRII, and the nucleotide sequence of the linker protein fragment ((G$_4$S)$_x$G) were obtained by conventional technique in the art. The C-terminal nucleotide of the anti-PD-L1 antibody was ligated through a linker protein to the N-terminal nucleotide of the extracellular domain of TGF-βRII with different lengths by homologous recombination technique, and then cloned into the Phr-BsmbI vector. Recombinant PD-L1/TGF-β trap was expressed in 293 cells and purified as described in Example 2. The purified protein can be used in the experiments of the following examples.

Example 2: Purification of PD-L1/TGF-β Trap Fusion Protein

The cell culture medium was centrifuged at high speed, and the supernatant was collected, and the first step of purification was performed by affinity chromatography. The chromatographic medium was Protein A or a derived filler that interacts with Fc, such as GE's Mabselect. The equilibration buffer was 1×PBS (137 mmol/L NaCl, 2.7 mmol/L KCl, 10 mmol/L Na$_2$HPO$_4$, 2 mmol/L KH$_2$PO$_4$, pH 7.4). After equilibrating 5 column volumes, the cell supernatant was loaded for binding, and the flow rate was controlled so that the sample was allowed to remain on the column for ≥1 min. After the sample was loaded, the column was washed with 1×PBS (pH 7.4) until the A280 read-out was reduced to baseline. Then, the column was washed with 0.1 M glycine (pH 3.0) elution buffer, and the eluted peak was collected according to the A280 ultraviolet absorption peak, and the collected eluted sample was neutralized with 1 M Tris (pH 8.5).

The neutralized eluted sample was concentrated by ultrafiltration, and then subjected to size exclusion chromatography The buffer was 1×PBS, and the column was XK26/60 Superdex 200 (GE). The flow rate was controlled at 4 ml/min, the loading volume was less than 5 ml, and the target protein peak was pooled according to A280 ultraviolet absorption. The purity of the collected protein was greater than 95% as identified by SEC-HPLC, and was verified by LC-MS. The verified sample was aliquoted for use. The PD-L1/TGF-β trap was obtained.

The performance and benefits of the present invention are verified by biochemical test methods as indicated below.

Biological Activity Evaluation In Vitro

Test Example 1: In Vitro ELISA Detection of PD-L1/TGF-β Trap Binding to TGF-β1

The detection process is described as follows:
a. 96-well plates were coated with 100 µl/well of human TGF-β1 (8915LC, CST) at a concentration of 1 µg/ml at 4° C. overnight.
b. The wells were washed 3 times with 250 µl of 1×PBST, then 250 µl of 5% milk PBS was added for blocking at 37° C. for 2 hours.
c. The wells were washed 3 times with 250 µl of 1×PBST, the PD-L1/TGF-β trap was diluted by gradient dilution, then TGF-β trap and positive control were added, and incubated for 1 hour at 37° C.
d. The wells were washed 3 times with 250 µl 1×PBST,
e. 100 µl of Anti-human Fc antibody-HRP (1:4000) was added to each well and incubated for 40 minutes at 37° C.
f. 100 µl of TMB was added into each well, incubated for 10 minutes at room temperature, and the reaction was stopped by adding 100 µl of 1 M H2SO4.
g. The absorbance at 450 nm was measured on a microplate reader, and the data was analyzed by Graphpad Prism5.

The results of binding of the fusion protein to human TGF-β1 in vitro are shown in FIGS. 2 and 3. The ELISA showed that fusion protein 1 in Table 2 did not retain the binding activity to human TGF-β1. Mass spectrometry analysis showed that fusion protein 1 (i.e., the non-truncated form of extracellular domain of TGF-βRII (1-136)) was unstable, and it was easy to break in the heavy chain TGF-βRII, and the positive control had the same defect. The fusion proteins comprising the N-terminal truncated form of the extracellular domain of TGFβRII, such as fusion proteins 7, 9, 10, 12-15, are specific for binding to human TGF-β1.

Test Example 2: In Vitro ELISA Detection of PD-L1/TGF-β Trap Binding to PD-L1

Antigen Used for Detection: PD-L1-his

SEQ ID NO: 17
FTVTVPKDLYVVEYGSNMTIECKFPVEKQLDLAALIVYWEMEDKNIIQ

FVHGEEDLKVQHSSYRQRARLLKDQLSLGNAALQITDVKLQDAGVYRC

MISYGGADYKRITVKVNAPYNKINQRILVVDPVTSEHELTCQAEGYPK

AEVIWTSSDHQVLSGKTTTTNSKREEKLFNVTSTLRINTTTNEIFYCT

FRRLDPEENHTAELVIPELPLAHPPNEREQKLISEEDLHHHHHH

The detection process is described as follows:
a. 96-well plates were coated with 100 µl/well of human PD-L1-His (SEQ ID NO: 17) at a concentration of 5 µg/ml at 4° C. overnight.
b. The wells were washed 3 times with 250 µl of 1×PBST, 250 µl of 5% milk PBS was added for blocking at 37° C. for 2 hours.
c. The wells were washed 3 times with 250 µl of 1×PBST, the PD-L1/TGF-β trap was diluted by gradient dilution, anti-PD-L1 antibody was added as a positive, and incubated for 1 hour at 37° C.
d. The wells were washed 3 times with 250 µl 1×PBST.

e. 100 μl of Anti-human Fc antibody-HRP (1:4000) was added into each well and incubated for 40 minutes at 37° C.

f. 100 μl of TMB as added into each well, incubated for 10 minutes at room temperature, and the reaction was stopped by adding 100 μl of 1 M $H_2SO_4$.

g. The absorbance at 450 nm was measured on a microplate reader, and the data was analyzed by Graphpad Prism5.

The results of binding of the fusion protein of the present invention to human PD-L1 in vitro are shown in FIG. 4. The ELISA showed that all fusion proteins retained the binding activity to human PD-L1.

Test Example 3: Blocking Detection of PD-1/PD-L1 In Vitro

1. Testing Purpose:

In order to investigate the blocking effect of PD-L1/TGF-β trap on the PD-1/PD-L1 signaling pathway, a cell-based antibody blocking experiment was performed on cells carrying human PD-1 and PD-L1 receptor molecules which were constructed by Promega, respectively.

2. Testing Samples

① PD-L1 antibody: SEQ ID NO: 11, SEQ ID NO: 12;

② Control 1 (20T-Fc): ECD(20-136)-Fc, a fusion protein comprising truncated TGF-βRII extracellular domain fragment ECD (20-136) and Fc Sequence is as follows:

```
SEQ ID NO: 18:
GAVKFPQLCKFCDVRFSTCDNQKSCMSNCSITSICEKPQEVCVAVWRK

NDENITLETVCHDPKLPYHDFILEDAASPKCIMKEKKKPGETFFMCSC

SSDECNDNIIFSEEYNTSNPDAESKYGPPCPPCPAPEAAGGPSVFLFP

PKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHY

TQKSLSLSLG
```

③ Control 2 (22T-Fc): ECD(22-136)-Fc, a fusion protein comprising truncated TGF-βRII extracellular domain fragment ECD (22-136) and Fc Sequence is as follows:

```
SEQ ID NO: 19:
VKFPQLCKFCDVRFSTCDNQKSCMSNCSITSICEKPQEVCVAVWRKND

ENITLETVCHDPKLPYHDFILEDAASPKCIMKEKKKPGETFFMCSCSS

DECNDNIIFSEEYNTSNPDAESKYGPPCPPCPAPEAAGGPSVFLFPPK

PKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQ

KSLSLSLG
```

④ Fusion protein 9, fusion protein 15;

⑤ human IgG: blank control, human immunoglobulin obtained from mixed normal human serum by purification using a conventional affinity chromatography method such as Protein A;

⑥ Positive control (M7824, prepared by reference patent WO2015118175): PD-L1 antibody/TGF-βRII extracellular domain fusion protein;

Light chain amino acid sequence of PD-L1 antibody:

```
SEQ ID NO: 20
QSALTQPASVSGSPGQSITISCTGTSSDVGGYNYVSWYQQHPGKAPKL

MIYDVSNRPSGVSNRFSGSKSGNTASLTISGLQAEDEADYYCSSYTSS

STRVFGTGTKVTVLGQPKANPTVTLFPPSSEELQANKATLVCLISDFY

PGAVTVAWKADGSPVKAGVETTKPSKQSNNKYAASSYLSLTPEQWKSH

RSYSCQVTHEGSTVEKTVAPTECS
```

H chain amino acid sequence of anti-PD-L1 antibody heavy chain/TGF-βRII extracellular domain (1-136):

```
SEQ ID NO: 21
EVQLLESGGGLVQPGGSLRLSCAASGFTFSSYIMMWVRQAPGKGLEWV

SSIYPSGGITFYADTVKGRFTISRDNSKNTLYLQMNSLRAEDTAVYYC

ARIKLGTVTTVDYWGQGTLVTVSSASTKGPSVFPLAPSSKSTSGGTAA

LGCLVKDYFPEPVTVSWNSGALTSGVHTFPAVLQSSGLYSLSSVVTVP

SSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEW

ESNGQPENNYKTTPPVLDSDGSFFLYSKLTVDKSRWQQGNVFSCSVMH

EALHNHYTQKSLSLSPGAGGGGSGGGGSGGGGSGGGGSGIPPHVQKSV

NNDMIVTDNNGAVKFPQLCKFCDVRFSTCDNQKSCMSNCSITSICEKP

QEVCVAVWRKNDENITLETVCHDPKLPYHDFILEDAASPKCIMKEKKK

PGETFFMCSCSSDECNDNIIFSEEYNTSNPD.
```

3. Testing Process

CHO/PD-L1 cells (CS187108, Promega) were digested and resuspended in F-12 Nutrient Mixture (Ham) complete medium. The cell density was adjusted to 4×10⁵/mL using complete medium according to the cell count results. The cell suspension was transferred to the loading tank, added to the 96-well plate at 100 μL/well using a multi-channel pipette, and incubated at 37° C., 5% $CO_2$ incubator for 20-24 h; The Jurkat/PD-1 (CS187102, Promega) cell suspension was prepared the next day, and the cells were resuspended according to the cell count results using assay medium, and the cell density was adjusted to 1.25×10⁶/mL. The cell culture plates comprising CHO/PD-L1 cells were taken out from the incubator, 95 μL of the culture solution was taken out per well using a multi-channel pipette, and the gradient-diluted fusion protein, anti-PD-L1 antibody and positive coontrol (M7824) were respectively added at 40 μL/well. Then the Jurkat/PD-1 cell suspension was transferred to a loading tank, added to the cell culture plate at 40 μL/well, and incubated at 37° C., 5% $CO_2$ for 5-6 h. During the incubation with protein, the Bio-Glo™ Reagent was taken out and allowed to return to room temperature. The cell culture plates were placed at room temperature for 5-10 min. Then 40 μL Bio-Glo™ Reagent was added to each well, incubated in a safety cabinet for 5-10 min, and the chemiluminescence signal value was read using a multi-function microplate reader.

4. Results

As shown in FIG. 5, just like the positive control molecule, the fusion protein 9 of the present invention was able to effectively block the binding of PD-1-expressing Jurkat cells to CHO/PD-L1 cells, and took effect in a dose-dependent manner along with drug concentration. Fusion protein 15 has the same blocking ability as that of fusion protein 9.

Test Example 4: Binding Affinity and Kinetics Detection In Vitro by Biacore

The affinity of the test molecule to human or murine TGF-β1 or human PD-L1 protein was determined by Biacore T200 (GE). The experimental procedure is described as follows:

A certain amount of PD-L1/TGF-β trap was captured with Protein A chip, and then the human or murine TGF-β1 (8915LC, CST) or human PD-L1 (Sino Biological) was flowed through the surface of the chip. The reaction signal was detected in real-time using Biacore to obtain the association and dissociation curves. The biochip was then washed and regenerated with glycine-hydrochloric acid (pH 1.5, GE). The buffer solution used in the experiment was HBS-EP Buffer (GE). The experimental data were fitted to (1:1) Langmuir model using BIAevaluation version 4.1 software (GE), and the affinity values were obtained, and are shown in Table 3.

TABLE 3

Affinity of fusion proteins of the invention to TGF-βI or human PD-L1 in virto

| Fusion protein* | Affinity sample | ka (1/Ms) | kd (1/s) | KD (M) |
|---|---|---|---|---|
| Fusion protein 9 | Human TGF-β1 | 1.73E7 | 7.28E−4 | 4.22E−11 |
| Fusion protein 15 |  | 2.69E7 | 6.08E−4 | 2.26E−11 |
| Fusion protein 9 | murine TGF-β1 | 4.33E7 | 1.33E−3 | 3.07E−11 |
| Fusion protein 15 |  | 3.57E7 | 1.22E−3 | 3.42E−11 |
| Fusion protein 9 | human PD-L1 | 1.97E6 | 1.24E−4 | 6.31E−11 |
| Fusion protein 15 |  | 2.00E6 | 1.24E−4 | 6.10E−11 |

*Fusion protein form is shown in Table 2.

The fusion protein binding activity is shown in Table 3. The results indicate that the fusion proteins 9 and 15 of the present invention have extremely high affinity to human and murine TGF-β1 and human PD-L1.

Test Example 5: SMAD3 Reporter Gene Inhibition Assay

1. Testing Purpose:

In this experiment, the Smad3 binding element (SBE) with luciferase reporter gene was expressed in HepG2 cells to study the inhibitory effect of PD-L1/TGF-β trap on TGF-β1-induced Smad3 activation, and the activity of PD-L1/TGF-β trap in vitro was evaluated according to IC50 value.

2. Test Sample: fusion protein 9, positive control (M7824)

3. Testing Process

HepG2 cells were cultured in MEM complete medium (GE, SH30243.01) containing 10% FBS and passaged every 3 days. On the first day of the experiment, 25,000 cells per well were inoculated on 96-well plates (Corning, 3903), and cultured at 37° C., 5% $CO_2$ for 24 hours. On the next day, the medium in the cell culture plates was discarded, and 100 ng of 3TP-Lux plasmid was transfected per well. The cells were further cultured at 37° C., 5% $CO_2$ for 24 hours. Six hours before the addition of the test sample, the complete medium in the 96-well plate was discarded, and 80 μL of incomplete medium (MEM+0.5% FBS) was added to each well. After 6 hours, 10 μL of human TGF-β1 (R&D, 240-B-010) solution, prepared in incomplete medium (final concentration of 2 ng/mL), and 10 μL of the test sample (the final concentration is 500, 50, 5, 0.5, 0.05, 0.005, 0.0005 and 0 nM) were added. The human TGF-β1 solvent was used as a control. The cells were cultured at 37° C., 5% $CO_2$ for another 18 h. Then, 100 μL of the prepared luciferase substrate ONE-Glo™ Luciferase Assay system (Promega, E6110) was added to each well, and incubated at room temperature for 10 minutes in darkness. Then the luminescent signal value was read using a Victor3 multi-plate reader (Perkin Elmer). The IC50 value of the test sample was calculated using the data software Graphpad Prism 5.0.

FIG. 6 shows that fusion protein 9 inhibits TGFβ-induced pSMAD3 activity in a dose-dependent manner, and has comparable efficacy and IC50 (concentration required to inhibit 50% of maximum activity) to that of positive control M7824. The test results of the anti-PD-L1 antibody showed that it had no inhibitory effect (IC50>500 nM).

Test Example 6: In Vitro Detection of IFNγ Secretion by PBMC Due to Tuberculin (TB) Stimulation 1. Test Purpose To investigate the activation of T lymphocytes by PD-L1/TGF-β trap, human peripheral blood mononuclear cells (PBMC) were collected and purified, and the secretion of IFNγ was detected after stimulation with tuberculin (TB) for 5 days.

2. Test Sample

① Human IgG; ② PD-L1 antibody; ③ Fusion protein 9 ④ control 1 (20T-Fc): ECD(20-136)-Fc; 5○ PD-L1 antiboy+control 1 (20T-Fc).

3. Test Process:

15 ml of purified fresh PBMC, about 3×10⁷ cells, with 20 μL of tuberculin added thereto, were cultured in an incubator for 5 days at 37° C., 5% $CO_2$. On day 6, the cultured cells were collected and centrifuged, washed once with PBS and resuspended in fresh medium with the density adjusted to of 1×10⁶ cell/ml. Then 90 μl of resuspended cells were added into the 96-well plate. 10 μL/well of different concentrations of antibodies were separately added to corresponding wells of the above 96-well cell culture plate. 10 μl PBS was added in the control and blank group, respectively. Then, the cell culture plate was incubated in the incubator for three days at 37° C., 5% $CO_2$. The cell culture plate was taken out, and the supernatant was taken from each well after centrifugation (4000 rpm, 10 min). After 10-fold dilution, the secretion of IFN-γ was detected by ELISA (human IFN-γ detection kit, Xinbosheng, EHC 102g.96), refer to the reagent instructions for specific operations. As shown in the FIG. 7, the PD-L1/TGF-β trap fusion protein samples were able to enhance the secretion of cytokine IFN-γ by activated T lymphocytes, and had a drug concentration dose effect.

TABLE 4

| Antibody | EC50 (nM) | Maximum secretion of IFNγ (pg/ml) | Minimal secretion of IFNγ (pg/ml) | Fold (secretion of IFNγ) |
|---|---|---|---|---|
| PD-L1 antibody | 0.05 | 2684 | 737 | 3.6 |
| Fusion protein 9 | 0.12 | 3422 | 638 | 5.4 |
| Control 1(20T-Fc) | >50 | 780 | 490 | 1.6 |
| PD-L1antibody + control 1 | 0.054 | 2879 | 746 | 3.9 |
| Human IgG | >50 | 375 | 298 | 1.2 |
| Blank control | / | 536 | 536 | 1 |

4. Result

As shown in FIG. 7 and Table 4, the fusion protein 9 was able to enhance the activated T lymphocyte to secrete cytokine IFN-γ in dose-dependent manner, and had a stronger activation effect than that of the anti-PD-L1 antibody and 20T-FC.

Pharmacokinetic Evaluation

Test Example 7

Three SD rats, female, were purchased from Jiesijie Experimental Animal Co., Ltd. and maintained in 12/12-hour light-dark cycle (the temperature is 24±3° C., the relative humidity is 50-60%), the rats had free access to water and diet. On the day of the experiment, SD rats were injected with the fusion protein in the tail vein at a dose of 6 mg/kg and an injection volume of 5 ml/kg.

Blood was collected at the following time points: 15 min, 7 h (on the first day), 24 h ($2^{nd}$ day), $3^{rd}$ day, $4^{th}$ day, $6^{th}$ day, $8^{th}$ day, $10^{th}$ day, and $15^{th}$ day after administration. 200 μl blood (equivalent to 100 μl serum) was taken from the fundus vein of the rat. The blood sample was placed at room temperature for 30 min to allow agglutination, and then centrifuged at 10000 g for 10 minutes at 4° C. The supernatant was taken and stored at −80° C. immediately. The concentration of the fusion protein in the serum was measured by ELISA.

The measure process is described as follows:

a. 96-well plates were coated with 100 μl/well of human PD-L1-His at a concentration of 2 μg/ml, overnight at 4° C.

b. The wells were washed 4 times with 250 μl of 1×PBST, then 250 μl of 5% milk PBS was added for blocking at 37° C. for 3 hours.

c. The wells were washed 4 times with 250 μl of 1×PBST, then 100 μl of the gradient-diluted serum sample was added, and incubated at 37° C. for 1 hour, with fusion protein 9 serving as a positive control.

d. The wells were washed 5 times with 250 μl 1×PBST.

e. 100 μl/well of biotinylated anti-human TGF-βRII antibody (R&D) was added, and incubated for 1 hour at 37° C.

f. The wells were washed 5 times with 250 μl 1×PBST.

g. 100 μl/well of TMB was added, incubated for 10 minutes at room temperature, and the reaction was stopped by adding 100 μl of 1 M $H_2SO_4$.

h. The absorbance at 450 nm was measured on a microplate reader, and the data was analyzed by Graphpad Prism5.

TABLE 5

| T½ of fusion protein in rat | | |
|---|---|---|
| Test drug | Administration mode | T½ (Mean ± SD, h) |
| Fusion protein 9 | IV (6 mg/kg) | 236 ± 10 |

The results of PK analysis indicated that the half-life of the fusion protein 9 of the present invention in rats was about 236 h (9.8 days), see Table 5.

Biological Activity Evaluation In Vivo

Test Example 8: Effect of PD-L1/TGF-β Trap on Murine Subcutaneous Xenograft of Human Breast Cancer MDA-MB-231

The murine strain used in this experiment was a NOD/SCID female mouse (Cavens). The human peripheral blood mononuclear cells used in the experiment were extracted from freshly collected blood, and the extraction method was as follows: The heparin anticoagulated venous blood was mixed with PBS containing 2% FBS in the same volume. After mixing, 25 ml of the diluted blood was slowly added to a centrifuge tube containing 15 ml of lymphocyte separation solution, and centrifuged at 1200 g for 10 minutes at room temperature. The lymphocyte layer was pipetted to another centrifuge tube, and cells were washed by PBS and centrifuged at 300 g for 8 minutes at room temperature. After repeating once, the cells were resuspended in RPMI-1640 medium containing 10% FBS, and the cells were added to a 6-well plate pre-coated with CD3 antibody (OKT3, 40 ng/ml) at $2×10^6$ cells/well (2 ml), and then placed in a 37° C. incubator for 4 days.

Test Sample:

① blank control: PBS; ② fusion protein 9-4.8mpk; ③ fusion protein 9-24mpk; ④ PD-L1 antibody-4mpk; ⑤ PD-L1 antibody-20mpk; ⑥ PD-L1 antibody-4mpk+control 1 (20T-Fc)-2.14mpk; ⑦ control 1 (20T-Fc)-2.14mpk.

MDA-MB-231 cells were resuspended in serum-free RPMI-1640 medium, and mixed with an equal volume of Matrigel. 100 μl ($2.3×10^6$ cells) was inoculated subcutaneously into the right flank of NOD/SCID mice. 11 days later, animals bearing oversized or undersized tumor were excluded, and mice were randomized into groups, with 9 animals in each group. $5×10^5$ stimulated PBMCs (60 μl) were injected into the tumor tissues, and the remaining PBMCs were further cultivated free of stimulation. One week later, $5×10^6$ PBMCs (100 μl) were intraperitoneally injected into tumor-bearing mice, as the first round of injection. Throughout the experimental period, for 2 and a half rounds, a total of 5 PBMC injections were provided. On the day of the first intratumoral injection, intraperitoneal administration was performed, three times a week for a total of 14 administrations. The administration regimen is shown in Table 6. The tumor volume and weight were measured twice a week. The experimental results are shown in Table 7.

TABLE 6

Test grouping and administration

| Group | Administration Dose |
|---|---|
| ① Blank control: PBS | 0 |
| ② Fusion protein 9-4.8 mpk | 4.8 mg/kg |
| ③ Fusion protein 9-24 mpk | 24 mg/kg |
| ④ PD-L1 antibody-4 mpk | 4 mg/kg |
| ⑤ PD-L1 antibody -20 mpk | 20 mg/kg |
| ⑥ PD-L1 antibody-4 mpk + control 1-2.14 mpk | 4 mg/kg + 2.14 mg/kg |
| ⑦ control 1-2.14 mpk | 2.14 mg/kg |

TABLE 7

Effect of fusion protein 9 on murine subcutaneous xenograft of MDA-MB-231

| Group | Day 0 Mean ± SEM (V mm³) | Day 25 Mean ± SEM (V mm³) | Day 25 % TGI | Day 32 Mean ± SEM (V mm³) | Day 32 % TGI | Day 33 Mean ± SEM (TW g) | Day 33 P (vs PBS) (TW) |
|---|---|---|---|---|---|---|---|
| ① Blank control: PBS | 62.5 ± 2.9 | 623.4 ± 43.3 | — | 941.1 ± 54.9 | — | 0.859 ± 0.063 | — |
| ② Fusion protein 9-4.8 mpk | 62.6 ± 3.5 | 414.6 ± 17.1*** | 37.24% | 618.9 ± 28.7*** | 36.68% | 0.454 ± 0.025*** | 2.06E−05 |
| ③ Fusion protein 9-24 mpk | 62.7 ± 3.3 | 329.8 ± 22.5*** | 52.38% | 495.3 ± 42.6*** | 50.76% | 0.367 ± 0.026*** | 2.20E−06 |
| ④ PD-L1 antibody - 4 mpk | 63.1 ± 3.5 | 454.4 ± 40.8* | 30.24% | 722.8 ± 65.8* | 24.91% | 0.592 ± 0.052** | 0.0050 |
| ⑤ PD-L1 antibody - 20 mpk | 62.6 ± 3.3 | 466.4 ± 17.2** | 28.01% | 741.8 ± 32.9** | 22.70% | 0.650 ± 0.033** | 0.0100 |
| ⑥ PD-L1 antibody - 4 mpk + control 1-2.14 mpk | 62.6 ± 3.3 | 447.5 ± 29.6** | 31.38% | 669.2 ± 45.3** | 30.96% | 0.566 ± 0.039** | 0.0012 |
| ⑦ control 1-2.14 mpk | 60.7 ± 3.3 | 601.5 ± 30.9 | 3.58% | 861.7 ± 34.2 | 8.83% | 0.652 ± 0.041* | 0.0178 |

Note:
Day 0: time for the first administration;
*p < 0.05
**p < 0.01
***p < 0.001,
compared with PBS by Student's t test.

The results are shown in FIG. 8. Antibody fusion protein 9 (4.8, 24 mg/kg) can significantly inhibit the growth of murine subcutaneous xenograft of human breast cancer MDA-MB-231. There was a dose-dependent relationship between high and low doses, and it was superior to reference drug anti-PD-L1 antibody (4, 20 mg/kg), TGF-βRII control molecule 20T-FC (2.14 mg/kg) and the combination group (PD-L1 antibody −4 mg/kg+20 T-FC−2.14 mg/kg) at equivalent molar dose, respectively. Each dose of fusion protein 9 maintained an ideal anti-tumor effect since the 14$^{th}$ day after administration; when compared with anti-PD-L1 antibody-20mpk, fusion protein 9 at high dose has obvious advantage (p<0.05). On the 25th days after administration, the anti-tumor effect of each antibody reached optimum level. The inhibition rates achieved by the group of fusion protein 9 combined with anti-PDL-1 antibody (at both high and low dose) were 37.24%, 52.38%, 30.24%, 28.01%, and 31.38%, respectively. Thirty-two days after administration, the anti-tumor effect of fusion protein 9 was still very significant. The tumor growth inhibition (% TGI) of the low and high dose group was 36.68% and 50.76%, respectively, and the tumor volume was statistically different, when compared with the control group (p<0.05).

Test Example 9: Physical Stability of PD-L1/TGF-β Trap

This test example was used to detect the stability of fusion protein 9 and fusion protein 15.

DSC (Differential scanning calorimetry) was used to detect the thermal stability of different antibodies, and the stability in different buffer systems was compared. Buffer systems comprise 10 mM acetate/135 mM NaCl (pH 5.5) and 10 mM acetate/9% trehalose (pH 5.5).

The sample was dissolved in the corresponding buffers, and the concentration was controlled at about 50 mg/ml. The detection was performed by MicroCal* VP-Capillary DSC (Malvern). Prior to testing, each sample and blank buffer was degassed for 1 to 2 min using a vacuum degassing device. Each well of the plate was added with 400 μl sample or blank buffer (the loading quantity was 300 μl). Finally, two pairs of well-plates were added with 14% Decon 90 and ddH$_2$O, respectively, and were ready to wash. The sample was loaded on the plate, and then the plate was sealed with a plastic cover. Scanning began with a temperature at 25° C. and ended at 100° C., and the scanning rate was 60° C./h. The results are shown in Table 8, indicating that both fusion protein 9 and fusion protein 15 show good thermal stability in these two test systems.

TABLE 8

| Sample | Buffer | Tm-onset (° C.) | TM (° C.) |
|---|---|---|---|
| Fusion protein 9 | 10 mM acetate/135 mM NaCl | 57.99 | 66.33 |
|  | 10 mM acetate/9% trehalose | 58.64 | 67.83 |
| Fusion protein 15 | 10 mM acetate/135 mM NaCl | 57.33 | 66.17 |
|  | 10 mM acetate/9% trehalose | 57.41 | 67.44 |

The periodic stability at certain concentrations was investigated by monitoring purity via SEC-HPLC, exemplary conditions, for example, the concentration of the sample was controlled at about 50 mg/ml. The stability of different antibodies in 10 mM acetate/135 mM NaCl (pH5.5) was compared under conditions such as 5 cycles of freezing and thawing at −80° C. and storing at 40° C. for one month.

Xbridge protein BEH SEC 200A (Waters) HPLC column was used for detection. The result is shown in Table 9 as follows. These two fusion proteins showed good stability.

TABLE 9

|  | fusion protein 9(Δ %) | fusion protein 15(Δ %) |
|---|---|---|
| 40° C. | 3.39% | 1.8% |
| −80° C. freeze-thaw | 1.44% | 1.39% |

Note:
Δ % indicates the rate of change.

Test Example 10: Chemical Stability of Fusion Protein

Deamidation is a common chemical modification which will influence the stability of an antibody in later stages. Especially, over-deamidation of amino acids in CDR regions should be avoided, and reduction of mutations in these regions is preferred. 1600 µg of the antibody to be tested was dissolved in 200 µl 10 mM acetate/135 mM NaCl (pH5.5), and placed in a 40° C. incubator. Samples were taken on day 0, 14 and 28 for an enzymatic hydrolysis assay. 100 µg of each sample taken at different time points was dissolved in 100µl 0.2 M His-HCl, 8 M Gua-HCl solution, pH 6.0. 3 µl 0.1 g/mL DTT was added, and then the sample was incubated in a 50° C. water bath for 1 hour. Then the sample was ultrafiltrated two times with 0.02M His-HCl (pH 6.0), and digested overnight at 37° C. in a water bath by adding 3 µL 0.25 mg/mL trypsin. The deamidation modification was examined using an Agilent 6530 Q-TOF LC-MS, and the results are shown in Table 10 below.

TABLE 10

| Sample | Heavy chain | Modification site | Day 0 | Day 14 | Day 28 |
|---|---|---|---|---|---|
| Fusion protein 9 | Heavy chain | N314 | 2.38% | 2.28% | 2.45% |
|  | Heavy chain | N324 | 0.20% | 3.60% | 7.88% |
| Fusion protein 15 | Heavy chain | N314 | 2.87% | 2.86% | 2.87% |
|  | Heavy chain | N324 | 0.00% | 3.61% | 7.93% |

Note:
N represents the detectable modified asparagine, and the number represents the position in the light chain or heavy chain from the N-terminus. The percent content represents the ratio of deamidation modifications detected by LC-MS to the signal of all peptides at that site.

The results of mass spectrometry showed that the two fusion proteins don't have obvious deamidation modification sites, suggesting that the fusion proteins have good chemical stability.

The invention claimed is:

1. A fusion protein having the general formula (I):

Ab-L-TGF-βRII ECD    (I)

wherein:
TGF-βRII ECD represents an N-terminal truncated form of the extracellular domain of TGF-βRII having a deletion of 14-26 contiguous amino acids at the N-terminus of the extracellular domain of TGF-βRIL wherein the extracellular domain of TGF-βRII comprises the amino acid sequence of SEQ ID NO: 13;

Ab represents an anti-PD-L1 antibody or antigen-binding fragment thereof, comprising:

HCDR1 of SEQ ID NO: 1;
HCDR2 of SEQ ID NO: 2;
HCDR3 of SEQ ID NO: 3;
LCDR1 of SEQ ID NO: 4;
LCDR2 of SEQ ID NO: 5; and
LCDR3 of SEQ ID NO: 6; and L represents a linker.

2. The fusion protein according to claim 1, wherein the N-terminal truncated form of the extracellular domain of TGF-βRII comprises a deletion of 14-21 contiguous amino acids at the N-terminus of the extracellular domain of TGF-βRII.

3. The fusion protein according to claim 1, wherein the anti-PD-L1 antibody or antigen-binding fragment thereof is selected from the group consisting of a full length antibody, a chimeric antibody, Fab', Fab, F(ab')$_2$, Fv, scFv, a bi-specific antibody, and a tri-specific antibody or mixture thereof.

4. The fusion protein according to claim 1, wherein the anti-PD-L1 antibody or antigen-binding fragment thereof is a chimeric antibody or a functional fragment thereof, .

5. The fusion protein according to claim 4, wherein the anti-PD-L1 antibody or antigen-binding fragment thereof is thea humanized antibody comprising a heavy chain variable region having the amino acid sequence of SEQ ID NO: 7.

6. The fusion protein according to claim 4, wherein the anti-PD-L1 antibody or antigen-binding fragment thereof is thea humanized antibody comprising a heavy chain having the amino acid sequence of SEQ ID NO: 11.

7. The fusion protein according to claim 4, wherein the anti-PD-L1 antibody or antigen-binding fragment thereof is mea humanized antibody comprising a light chain variable region having the amino acid sequence of SEQ ID NO: 8 or SEQ ID NO: 10.

8. The fusion protein according to claim 4, wherein the anti-PD-L1 antibody or antigen-binding fragment thereof is mea humanized antibody comprising a light chain having the amino acid sequence of SEQ ID NO: 12.

9. The fusion protein according to claim 1, wherein the linker has the amino acid sequence of $(G_4S)xG$, wherein x is an integer of 3-6.

10. The fusion protein according to claim 1, wherein the N-terminal truncated form of the extracellular domain of TGF-βRII consists of an amino acid sequence selected from the group consisting of SEQ ID NO: 14 and SEQ ID NO: 15, and Ab represents the anti-PD-L1 antibody having the heavy chain sequence of SEQ ID NO: 11 and the light chain sequence of SEQ ID NO:12.

11. The fusion protein according to claim 1, wherein the N-terminal truncated form of the extracellular domain of TGF-βRII consists of an amino acid sequence selected from the group consisting of SEQ ID NO: 14, SEQ ID NO: 15, and SEQ ID NO: 16.

12. The fusion protein according to claim 11, wherein the anti-PD-L1 antibody or antigen-binding fragment thereof comprises a heavy chain variable region having the amino acid sequence of SEQ ID NO:9, and a light chain variable region having the amino acid sequence of SEQ ID NO: 8 or SEQ ID NO: 10.

13. The fusion protein according to claim 11, wherein the N-terminal truncated form of the extracellular domain of TGF-βRII is fused to the carboxy terminus of the heavy chain of the anti-PD-L1 antibody via the linker.

14. A pharmaceutical composition, comprising a therapeutically effective amount of the fusion protein claim 1, and one or more pharmaceutically acceptable carrier(s), diluent(s) or excipient(s).

15. A method for treating a PD-L1-mediated tumor, comprising administering to a patient in need thereof a therapeutically effective amount of the fusion protein of claim 1.

16. The method according to claim 15, wherein the PD-L1-mediated tumor is selected from the group consisting of colorectal, breast, ovary, pancreas, stomach, prostate, kidney, cervix, thyroid, endometrium, uterus, bladder, neuroendocrine, head and neck, liver, nasopharynx, testis, small cell lung cancer, non-small cell lung cancer, dermatofibrosarcoma protuberans, Neck Cell carcinoma, glioblastoma, glioma, sarcoma, and mesothelioma.

* * * * *

SEQUENCE LISTING

```
<160> NUMBER OF SEQ ID NOS: 21

<210> SEQ ID NO 1
<211> LENGTH: 5
<212> TYPE: PRT
<213> ORGANISM: Mus musculus

<400> SEQUENCE: 1

Ser Tyr Trp Met His
1               5

<210> SEQ ID NO 2
<211> LENGTH: 17
<212> TYPE: PRT
<213> ORGANISM: Artificial sequence
<220> FEATURE:
<223> OTHER INFORMATION: PD-L1 antibody HCDR2 mutant
<220> FEATURE:
<221> NAME/KEY: MISC_FEATURE
<222> LOCATION: (3)..(3)
<223> OTHER INFORMATION: Xaa is His or Gly.
<220> FEATURE:
<221> NAME/KEY: MISC_FEATURE
<222> LOCATION: (8)..(8)
<223> OTHER INFORMATION: Xaa is Gly or Phe.

<400> SEQUENCE: 2

Arg Ile Xaa Pro Asn Ser Gly Xaa Thr Ser Tyr Asn Glu Lys Phe Lys
1               5                   10                  15

Asn

<210> SEQ ID NO 3
<211> LENGTH: 10
<212> TYPE: PRT
<213> ORGANISM: Mus musculus

<400> SEQUENCE: 3

Gly Gly Ser Ser Tyr Asp Tyr Phe Asp Tyr
1               5                   10
```

<210> SEQ ID NO 4
<211> LENGTH: 15
<212> TYPE: PRT
<213> ORGANISM: Mus musculus

<400> SEQUENCE: 4

```
Arg Ala Ser Glu Ser Val Ser Ile His Gly Thr His Leu Met His
1               5                   10                  15
```

<210> SEQ ID NO 5
<211> LENGTH: 7
<212> TYPE: PRT
<213> ORGANISM: Mus musculus

<400> SEQUENCE: 5

```
Ala Ala Ser Asn Leu Glu Ser
1               5
```

<210> SEQ ID NO 6
<211> LENGTH: 9
<212> TYPE: PRT
<213> ORGANISM: Mus musculus

<400> SEQUENCE: 6

```
Gln Gln Ser Phe Glu Asp Pro Leu Thr
1               5
```

<210> SEQ ID NO 7
<211> LENGTH: 119
<212> TYPE: PRT
<213> ORGANISM: Artificial sequence
<220> FEATURE:
<223> OTHER INFORMATION: PD-L1 antibody humanized heavy chian variable
      region mutant
<220> FEATURE:
<221> NAME/KEY: MISC_FEATURE
<222> LOCATION: (52)..(52)
<223> OTHER INFORMATION: Xaa is His or Gly.
<220> FEATURE:
<221> NAME/KEY: MISC_FEATURE
<222> LOCATION: (57)..(57)
<223> OTHER INFORMATION: Xaa is Gly or Phe.

<400> SEQUENCE: 7

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Arg Ile Xaa Pro Asn Ser Gly Xaa Thr Ser Tyr Asn Glu Lys Phe
        50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
                100                 105                 110

Thr Thr Val Thr Val Ser Ser
            115
```

<210> SEQ ID NO 8
<211> LENGTH: 111

<212> TYPE: PRT
<213> ORGANISM: Artifical sequence
<220> FEATURE:
<223> OTHER INFORMATION: PD-L1 antibody humanized light chain variable
      region

<400> SEQUENCE: 8

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
            100                 105                 110

<210> SEQ ID NO 9
<211> LENGTH: 119
<212> TYPE: PRT
<213> ORGANISM: Artificial sequence
<220> FEATURE:
<223> OTHER INFORMATION: Affinity matured PD-L1 antibody heavy chain
      variable region

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Gly Pro Asn Ser Gly Phe Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
            100                 105                 110

Thr Thr Val Thr Val Ser Ser
        115

<210> SEQ ID NO 10
<211> LENGTH: 111
<212> TYPE: PRT
<213> ORGANISM: Artificial sequence
<220> FEATURE:
<223> OTHER INFORMATION: Affinity matured PD-L1 antibody light chain
      variable region

<400> SEQUENCE: 10

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His

```
                    20                  25                  30
Gly Thr His Leu Met His Trp Tyr Gln Gln Lys Pro Gly Gln Pro
                35                  40                  45

Lys Leu Leu Ile Tyr Ala Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys
                100                 105                 110

<210> SEQ ID NO 11
<211> LENGTH: 446
<212> TYPE: PRT
<213> ORGANISM: Artificial sequence
<220> FEATURE:
<223> OTHER INFORMATION: PD-L1 antibody heavy chain

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Arg Ile Gly Pro Asn Ser Gly Phe Thr Ser Tyr Asn Glu Lys Phe
    50                  55                  60

Lys Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ser Tyr Asp Tyr Phe Asp Tyr Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
```

```
                275                 280                 285
Lys Pro Arg Glu Glu Gln Phe Asn Ser Thr Tyr Arg Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Ala
                435                 440                 445

<210> SEQ ID NO 12
<211> LENGTH: 218
<212> TYPE: PRT
<213> ORGANISM: Artificial sequence
<220> FEATURE:
<223> OTHER INFORMATION: PD-L1 antibody light chain

<400> SEQUENCE: 12

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Ile His
                20                  25                  30

Gly Thr His Leu Met His Trp Tyr Gln Gln Lys Pro Gly Gln Pro Pro
                35                  40                  45

Lys Leu Leu Ile Tyr Ala Ala Ser Asn Leu Glu Ser Gly Val Pro Ala
50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Phe
                85                  90                  95

Glu Asp Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
                130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
```

```
                    195                 200                 205

Val Thr Lys Ser Phe Asn Arg Gly Glu Cys
    210                 215

<210> SEQ ID NO 13
<211> LENGTH: 136
<212> TYPE: PRT
<213> ORGANISM: Homo sapiens
<220> FEATURE:
<223> OTHER INFORMATION: Sequence of TGF-beta RII extracellular domain:
      ECD(1-136)

<400> SEQUENCE: 13

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp
    130                 135

<210> SEQ ID NO 14
<211> LENGTH: 117
<212> TYPE: PRT
<213> ORGANISM: Artificial sequence
<220> FEATURE:
<223> OTHER INFORMATION: Sequence of truncated TGF-beta RII
      extracellular domain which involves a deletion of 19 contiguous
      amino acids at N-terminus: ECD(20-136)

<400> SEQUENCE: 14

Gly Ala Val Lys Phe Pro Gln Leu Cys Lys Phe Cys Asp Val Arg Phe
1               5                   10                  15

Ser Thr Cys Asp Asn Gln Lys Ser Cys Met Ser Asn Cys Ser Ile Thr
            20                  25                  30

Ser Ile Cys Glu Lys Pro Gln Glu Val Cys Val Ala Val Trp Arg Lys
        35                  40                  45

Asn Asp Glu Asn Ile Thr Leu Glu Thr Val Cys His Asp Pro Lys Leu
    50                  55                  60

Pro Tyr His Asp Phe Ile Leu Glu Asp Ala Ala Ser Pro Lys Cys Ile
65                  70                  75                  80

Met Lys Glu Lys Lys Pro Gly Glu Thr Phe Phe Met Cys Ser Cys
                85                  90                  95

Ser Ser Asp Glu Cys Asn Asp Asn Ile Ile Phe Ser Glu Glu Tyr Asn
        100                 105                 110

Thr Ser Asn Pro Asp
    115
```

<210> SEQ ID NO 15
<211> LENGTH: 115
<212> TYPE: PRT
<213> ORGANISM: Artificial sequence
<220> FEATURE:
<223> OTHER INFORMATION: Sequence of truncated TGF-beta RII
      extracellular domain which involves a deletion of 21 contiguous
      amino acids at N-terminus: ECD(22-136)

<400> SEQUENCE: 15

```
Val Lys Phe Pro Gln Leu Cys Lys Phe Cys Asp Val Arg Phe Ser Thr
1               5                   10                  15

Cys Asp Asn Gln Lys Ser Cys Met Ser Asn Cys Ser Ile Thr Ser Ile
                20                  25                  30

Cys Glu Lys Pro Gln Glu Val Cys Val Ala Val Trp Arg Lys Asn Asp
            35                  40                  45

Glu Asn Ile Thr Leu Glu Thr Val Cys His Asp Pro Lys Leu Pro Tyr
        50                  55                  60

His Asp Phe Ile Leu Glu Asp Ala Ala Ser Pro Lys Cys Ile Met Lys
65                  70                  75                  80

Glu Lys Lys Lys Pro Gly Glu Thr Phe Phe Met Cys Ser Cys Ser Ser
                85                  90                  95

Asp Glu Cys Asn Asp Asn Ile Ile Phe Ser Glu Glu Tyr Asn Thr Ser
                100                 105                 110

Asn Pro Asp
        115
```

<210> SEQ ID NO 16
<211> LENGTH: 122
<212> TYPE: PRT
<213> ORGANISM: Artificial sequence
<220> FEATURE:
<223> OTHER INFORMATION: Sequence of truncated TGF-beta RII
      extracellular domain which involves a deletion of 14 contiguous
      amino acids at N-terminus: ECD(15-136)

<400> SEQUENCE: 16

```
Val Thr Asp Asn Asn Gly Ala Val Lys Phe Pro Gln Leu Cys Lys Phe
1               5                   10                  15

Cys Asp Val Arg Phe Ser Thr Cys Asp Asn Gln Lys Ser Cys Met Ser
                20                  25                  30

Asn Cys Ser Ile Thr Ser Ile Cys Glu Lys Pro Gln Glu Val Cys Val
            35                  40                  45

Ala Val Trp Arg Lys Asn Asp Glu Asn Ile Thr Leu Glu Thr Val Cys
        50                  55                  60

His Asp Pro Lys Leu Pro Tyr His Asp Phe Ile Leu Glu Asp Ala Ala
65                  70                  75                  80

Ser Pro Lys Cys Ile Met Lys Glu Lys Lys Lys Pro Gly Glu Thr Phe
                85                  90                  95

Phe Met Cys Ser Cys Ser Ser Asp Glu Cys Asn Asp Asn Ile Ile Phe
                100                 105                 110

Ser Glu Glu Tyr Asn Thr Ser Asn Pro Asp
        115                 120
```

<210> SEQ ID NO 17
<211> LENGTH: 236
<212> TYPE: PRT
<213> ORGANISM: Artificial sequence
<220> FEATURE:
<223> OTHER INFORMATION: Antigen used for detection: PD-L1-His

<400> SEQUENCE: 17

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Glu Gln Lys Leu
    210                 215                 220

Ile Ser Glu Glu Asp Leu His His His His His
225                 230                 235
```

<210> SEQ ID NO 18
<211> LENGTH: 346
<212> TYPE: PRT
<213> ORGANISM: Artificial sequence
<220> FEATURE:
<223> OTHER INFORMATION: Control 1 (20T-Fc): ECD(20-136)-Fc, fusion protein comprising truncated TGF-beta RII extracellular domain fragment ECD (20-136) and Fc

<400> SEQUENCE: 18

```
Gly Ala Val Lys Phe Pro Gln Leu Cys Lys Phe Cys Asp Val Arg Phe
1               5                   10                  15

Ser Thr Cys Asp Asn Gln Lys Ser Cys Met Ser Asn Cys Ser Ile Thr
            20                  25                  30

Ser Ile Cys Glu Lys Pro Gln Glu Val Cys Val Ala Val Trp Arg Lys
        35                  40                  45

Asn Asp Glu Asn Ile Thr Leu Glu Thr Val Cys His Asp Pro Lys Leu
    50                  55                  60

Pro Tyr His Asp Phe Ile Leu Glu Asp Ala Ala Ser Pro Lys Cys Ile
65                  70                  75                  80

Met Lys Glu Lys Lys Lys Pro Gly Glu Thr Phe Phe Met Cys Ser Cys
                85                  90                  95

Ser Ser Asp Glu Cys Asn Asp Asn Ile Ile Phe Ser Glu Glu Tyr Asn
```

```
            100                 105                 110

Thr Ser Asn Pro Asp Ala Glu Ser Lys Tyr Gly Pro Pro Cys Pro Pro
        115                 120                 125

Cys Pro Ala Pro Glu Ala Ala Gly Gly Pro Ser Val Phe Leu Phe Pro
        130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
                180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
                260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Val Leu Asp Ser Asp Gly Ser Phe
        290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly
            340                 345

<210> SEQ ID NO 19
<211> LENGTH: 344
<212> TYPE: PRT
<213> ORGANISM: Artificial sequence
<220> FEATURE:
<223> OTHER INFORMATION: Control 2 (22T-Fc): ECD(22-136)-Fc, fusion
      protein comprising truncated TGF-beta RII extracellular domain
      fragment ECD (22-136) and Fc

<400> SEQUENCE: 19

Val Lys Phe Pro Gln Leu Cys Lys Phe Cys Asp Val Arg Phe Ser Thr
1               5                   10                  15

Cys Asp Asn Gln Lys Ser Cys Met Ser Asn Cys Ser Ile Thr Ser Ile
                20                  25                  30

Cys Glu Lys Pro Gln Glu Val Cys Val Ala Val Trp Arg Lys Asn Asp
            35                  40                  45

Glu Asn Ile Thr Leu Glu Thr Val Cys His Asp Pro Lys Leu Pro Tyr
        50                  55                  60

His Asp Phe Ile Leu Glu Asp Ala Ala Ser Pro Lys Cys Ile Met Lys
65                  70                  75                  80

Glu Lys Lys Lys Pro Gly Glu Thr Phe Phe Met Cys Ser Cys Ser Ser
                85                  90                  95

Asp Glu Cys Asn Asp Asn Ile Ile Phe Ser Glu Glu Tyr Asn Thr Ser
                100                 105                 110
```

Asn Pro Asp Ala Glu Ser Lys Tyr Gly Pro Pro Cys Pro Pro Cys Pro
            115                 120                 125

Ala Pro Glu Ala Ala Gly Gly Pro Ser Val Phe Leu Phe Pro Pro Lys
        130                 135                 140

Pro Lys Asp Thr Leu Met Ile Ser Arg Thr Pro Glu Val Thr Cys Val
145                 150                 155                 160

Val Val Asp Val Ser Gln Glu Asp Pro Glu Val Gln Phe Asn Trp Tyr
                165                 170                 175

Val Asp Gly Val Glu Val His Asn Ala Lys Thr Lys Pro Arg Glu Glu
            180                 185                 190

Gln Phe Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
210                 215                 220

Gly Leu Pro Ser Ser Ile Glu Lys Thr Ile Ser Lys Ala Lys Gly Gln
225                 230                 235                 240

Pro Arg Glu Pro Gln Val Tyr Thr Leu Pro Pro Ser Gln Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
290                 295                 300

Tyr Ser Arg Leu Thr Val Asp Lys Ser Arg Trp Gln Glu Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Leu Gly
            340

<210> SEQ ID NO 20
<211> LENGTH: 216
<212> TYPE: PRT
<213> ORGANISM: Artificial sequence
<220> FEATURE:
<223> OTHER INFORMATION: Light chain amino acid sequence of PD-L1
      antibody

<400> SEQUENCE: 20

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu

```
                115                 120                 125
Leu Gln Ala Asn Lys Ala Thr Leu Val Cys Leu Ile Ser Asp Phe Tyr
            130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser
    210                 215

<210> SEQ ID NO 21
<211> LENGTH: 607
<212> TYPE: PRT
<213> ORGANISM: Artificial sequence
<220> FEATURE:
<223> OTHER INFORMATION: H chain amino acid sequence of PD-L1 antibody
      heavy chain/TGF-beta RII extracellular domain

<400> SEQUENCE: 21

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ile Met Met Trp Val Arg Gln Ala Pro Gly Lys Gly Leu Glu Trp Val
        35                  40                  45
Ser Ser Ile Tyr Pro Ser Gly Gly Ile Thr Phe Tyr Ala Asp Thr Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ile Lys Leu Gly Thr Val Thr Thr Val Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260             265             270

Asp Pro Glu Val Lys Phe Asn Trp Tyr Val Asp Gly Val Glu Val His
        275                 280             285

Asn Ala Lys Thr Lys Pro Arg Glu Glu Gln Tyr Asn Ser Thr Tyr Arg
    290                 295             300

Val Val Ser Val Leu Thr Val Leu His Gln Asp Trp Leu Asn Gly Lys
305             310             315                 320

Glu Tyr Lys Cys Lys Val Ser Asn Lys Ala Leu Pro Ala Pro Ile Glu
            325                 330             335

Lys Thr Ile Ser Lys Ala Lys Gly Gln Pro Arg Glu Pro Gln Val Tyr
            340                 345             350

Thr Leu Pro Pro Ser Arg Glu Glu Met Thr Lys Asn Gln Val Ser Leu
            355                 360             365

Thr Cys Leu Val Lys Gly Phe Tyr Pro Ser Asp Ile Ala Val Glu Trp
            370             375             380

Glu Ser Asn Gly Gln Pro Glu Asn Asn Tyr Lys Thr Thr Pro Pro Val
385                 390             395                 400

Leu Asp Ser Asp Gly Ser Phe Phe Leu Tyr Ser Lys Leu Thr Val Asp
                405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Ala Gly Gly Gly Ser Gly Gly Gly Ser Gly Gly Gly
450                 455             460

Ser Gly Gly Gly Ser Gly Ile Pro Pro His Val Gln Lys Ser Val
465             470             475             480

Asn Asn Asp Met Ile Val Thr Asp Asn Asn Gly Ala Val Lys Phe Pro
            485             490             495

Gln Leu Cys Lys Phe Cys Asp Val Arg Phe Ser Thr Cys Asp Asn Gln
            500             505             510

Lys Ser Cys Met Ser Asn Cys Ser Ile Thr Ser Ile Cys Glu Lys Pro
            515             520             525

Gln Glu Val Cys Val Ala Val Trp Arg Lys Asn Asp Glu Asn Ile Thr
530             535             540

Leu Glu Thr Val Cys His Asp Pro Lys Leu Pro Tyr His Asp Phe Ile
545             550             555             560

Leu Glu Asp Ala Ala Ser Pro Lys Cys Ile Met Lys Glu Lys Lys
            565             570             575

Pro Gly Glu Thr Phe Phe Met Cys Ser Cys Ser Ser Asp Glu Cys Asn
            580             585             590

Asp Asn Ile Ile Phe Ser Glu Glu Tyr Asn Thr Ser Asn Pro Asp
            595             600             605
```